US006201021B1

(12) United States Patent
Ohuchida et al.

(10) Patent No.: US 6,201,021 B1
(45) Date of Patent: Mar. 13, 2001

(54) PENTANOIC ACID DERIVATIVES

(75) Inventors: Shuichi Ohuchida; Kazuo Kishimoto; Narito Tateishi; Hiroyuki Ohno, all of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 421 days.

(21) Appl. No.: 08/681,482

(22) Filed: Jul. 23, 1996

Related U.S. Application Data

(63) Continuation of application No. 08/252,642, filed on Jun. 1, 1994, now abandoned.

(30) Foreign Application Priority Data

| Jun. 1, 1993 | (JP) | 5-154331 |
| Nov. 5, 1993 | (JP) | 5-301067 |
| Mar. 28, 1994 | (JP) | 6-080982 |

(51) Int. Cl.$^7$ ............. A61K 31/19; A61K 31/192; A61K 31/20
(52) U.S. Cl. ............. 514/558; 514/557; 554/225; 562/493; 562/503; 562/512; 562/581; 562/588; 562/606
(58) Field of Search ............. 514/558, 557; 554/225

(56) References Cited

U.S. PATENT DOCUMENTS

| 3,325,361 | 6/1967 | Meunier | 167/65 |
| 4,025,649 | * 5/1977 | Taillandier et al. | 424/318 |
| 4,127,604 | * 11/1978 | Chignac et al. | 562/606 |
| 4,377,533 | * 3/1983 | Bouisset et al. | 260/465.1 |
| 5,672,746 | 9/1997 | Nau et al. | 562/598 |

FOREIGN PATENT DOCUMENTS

| 0252736 | 1/1988 | (EP) . |
| 6116200 | 4/1994 | (JP) | C07C/53/21 |

OTHER PUBLICATIONS

Journal of Geriatric Psychiatry and Neurology, "Sodium Valproate in the Treatment of Behavioral Disturbance in Dementia", vol. 6, Oct.–Dec. 1993.
Scientific American, pp. 44–52, Apr. 1989.
J. Anat., 106, 471 (1970) (Month Not Available).
Dev. Biol. 72, 381 (1979) (Month Not Available).
Adv. Cell. Neurobiol., 2, 249 (1981) (Month Not Available).
Science, 237, 642 (Aug. 1987).
Brain Res., 481, 190 (1989) (Month Not Available).
Ibid, 547, 223 (1991) (Month Not Available).
Cytobios., 61, 133 (1990) (Month Not Available).
Biochem. Biophys. Res. Commun., 136, 57 (Apr. 1986).
Brain Res., 560, 76 (1991) (Month Not Available).
Neuron., 3, 275 (1989) (Month Not Available).
J. Neurosci. Res., 25 431 (1990) (Month Not Available).
FEBS Lett., 292, 171 (Nov. 1991).
J. Neurol. Sci., 112, 68 (1991) (Month Not Available).
Proc. Natl. Acad. Sci. USA., 82, 4245 (Jun. 1985).
Brain Res. Reviews, 16, 83 (1991) (Month Not Available).
TIPS, 12, 383 (Oct. 1991).
Proc. Natl. Acad. Sci. USA, 87, 9020 (Nov. 1990).
Brain Res., 533, 315 (1990) (Month Not Available).
Neurology, 40, 33 (Jan. 1990).
Nikkei Sci. J., 9, 52 (1991) (Month Not Available).

(List continued on next page.)

Primary Examiner—Laura L. Stockton
(74) Attorney, Agent, or Firm—Sughrue, Mion, Zinn, Macpeak & Seas, PLLC

(57) ABSTRACT

Formula (I) compounds:

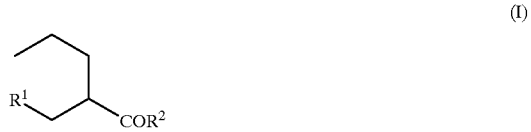

wherein $R^1$ is alkyl substituted by fluorine(s); $R^2$ is hydroxy, alkoxy, alkoxy substituted by phenyl, $NR^3R^4$, in which $R^3$, $R^4$ is (i) hydrogen, (ii) alkyl, (iii) phenyl, (iv) phenyl substituted by alkoxy or carboxyl, (v) heterocyclic ring containing nitrogen atom, (vi) alkyl substituted by phenyl, phenyl subsituted by alkoxy or carboxyl, heterocyclic ring containing nitrogen atom, (vii) the nitrogen bonded to $R^3$ and $R^4$, taken together is a saturated heterocyclic ring or amino acid residue; and non-toxic salts and acid addition salts thereof. Also, Formula (X) compounds:

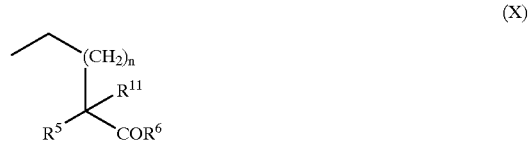

wherein n is 0 or 1, $R^{11}$ is hydrogen and chlorine, $R^5$ is $R^7$—$CH_2$— or $R^8$, or $R^5$ and $R^{11}$, taken together is alkylidene; $R^6$ is hydroxy, alkoxy, alkoxy substituted by phenyl, $NR^9R^{10}$, in which $R^9$, $R^{10}$ is (i) hydrogen, (ii) alkyl, (iii) phenyl, (iv) phenyl substituted by alkoxy or carboxyl, (v) heterocyclic ring containing nitrogen atom, (vi) alkyl substituted by phenyl, phenyl-substituted by alkoxy or carboxyl, heterocyclic ring containing nitrogen atom, (vii) the nitrogen bonded to $R^9$ and $R^{10}$, taken together is a saturated heterocyclic ring or amino acid residue, $R^7$ is (i) F—$(CH_2)$m— or $F_3C$—$CH_2$—, (ii) alkyl subsstituted by chlorine, (iii) alkyl substituted by alkoxy, cycloalkyl, phenyl, phenoxy; $R^8$ is alkyl, alkenyl, alkoxy, alkylthio, cycloalkyl, phenyl, phenoxy. Non-toxic and acid addition salts thereof are useful to prevent and/or treat neurodegenerative disease (e.g., Alzheimer's) and neuronal dysfunction by stroke or traumatic injury (e.g., Multiple sclerosis).

10 Claims, 1 Drawing Sheet

OTHER PUBLICATIONS

Neuropharmacology, 24(5), 427–435(1985) (Month Not Available).
Neuropharamcology, 25, 617 (1986) (Month Not Available).
Brain Res., 459, 131 (1988) (Month Not Available).
Brain Res., 554, 223 (1991) (Month Not Available).
Neurochem. Res., 17, 327 (1992) (Month Not Available).
Sciece, 250, 279 (Oct. 1990).
Neurobiol. Aging, 13, 239 (1992) (Month Not Available).
Chemical Abstracts, vol. 64, No. 7, Mar. 28, 1966.
Chemical Abstracts, vol. 82, No. 25, Jun. 23, 1975.
Chemical Abstracts, vol. 114, No. 1, Jan. 7, 1991.

* cited by examiner

PENTANOIC ACID DERIVATIVES

This is a Continuation of application Ser. No. 08/252,642 filed Jun. 1, 1994 now abandoned.

SUMMARY

This invention is related to pentanoic acid derivatives. More particularly, this invention is related to:

(1) pentanoic acid derivatives of the formula (1):

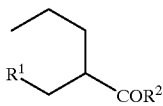

(I)

wherein all the symbols are the same meaning as hereafter defined, and non-toxic salts thereof and acid addition salts thereof, (2) improving agent of the brain functions containing pentanoic acid derivatives of the formula (I) and non-toxic salts thereof and acid addition salts thereof as active ingredient, (3) process for the preparation of pentanoic acid derivatives of the formula (I) and non-toxic salts thereof and acid addition salts thereof and (4) improving agent of the brain functions containing pentanoic acid derivatives of the formula (X):

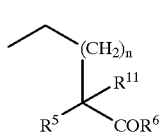

(X)

wherein all the symbols are the same meaning as hereafter defined, and non-toxic salts thereof and acid addition salts thereof as active ingredient.

BACKGROUND

The two major structural units that form the brain are neuron and glia. The neuron is composed of a cell body with dendrites. Ramified structures that transmit neuro-information along an axon and those receiving impulses via other neurons are the two types of dendrites known in existence. Neuro-information is conducted from one neuron to another via transmission across the synapse, a cleft that closely connects the dendrites of two communicating neurons.

However, glia is units that complement the functions of these neurons by supplying nutrients, eliminating catabolites/wastes, maintaining a proper ion equilibrium and performing other related functional roles for neurons to physiologically function normally. The glia encompass various types of cells. There are astrocytes, oligodendrocytes and microglia in the central nervous system; Schwann's and mantle cells in the peripheral nervous system; and ependymal cells in the ventricular endothelium.

The growth and differentiation of neurons prevail immediately before and after birth, whereas those of glia persist even after birth. The etiological factors of neurodegenerative diseases (such as Alzheimer's disease, multiple sclerosis, hepatic encephalopathy and delayed neuronal death) have been thought to be attributed mainly to abnormalities in the neurons. However, attention has recently been focused on the functional abnormalities of glia surrounding the neurons, especially astrocytes (Scientific American, pp45–52, April 1989). This is because astrocytes not only act as complementary cells, but they also promote the metabolism of glutamate and γ-amino butyrate (GABA), syntheses of neuropeptides and cytokines, and function as either immunocysts or neurons beside displaying important roles in regulating brain functions. As such, abnormalities in the astrocyte functions may be the determinant factors in inducing various brain-related diseases.

When encephalopathia occurred, reactive astrocytosis generated from astrocyte-derived reactive astrocytes agglutinate in the vicinity of sites where neurons die [J. Anat., 106, 471 (1970); Dev. Biol., 72, 381 (1979); Adv. Cell. Neurobiol., 2, 249 (1981)]. Although reactive astrocytosis eventuated in brain insults has been thought to be a compensatory response to neuronal regeneration, recent evidences have suggested that the excessive response of reactive astrocytosis triggers neurodegenerative decidua [Science, 237, 642 (1987); Brain Res., 481, 191 (1989); Ibid, 547, 223 (1991)]. From the participating reactive astrocytes in this excessive response, various neurotransmitters and cytokines are released [Cytobios., 61, 133 (1990)]. Of these, the most significant have been the identification of nerve growth factor (NGF) [Biochem. Biophys. Res. Commun., 136, 57 (1986); Brain Res., 560, 76 (1991)] and β-amyloid precursor protein (β-APP) secretions [Neuron., 3, 275 (1988); J. Neurosci. Res., 25, 431 (1990); FEBS Lett., 292, 171 (1991)]. The expression of β-APP has prompted reactive astrocytes as a possible source of β-amyloid, and the close relationship between β-amyloid deposits and reactive astrocytosis has since been implicated [J. Neurol. Sci., 112, 68 (1992)]. β-amyloid plagues display an important role in the induction of Alzheimer's disease (AD), a representative neurodegenerative disease [Proc. Natl. Acad. Sci. USA., 82, 4245 (1985); Brain Res. Reviews, 16, 83 (1991); TIPS, 12, 383 (1991)].

Based on the dose/efficacy relationship, NGF secreted from the reactive astrocytes elicits a neurotoxic activity $1.0 \times 10^5$-fold more potent than that of β-amyloid alone [Science, 250, 279 (1990)], and indicates a synergistic effect on β-amyloid-induced neuronal death [Proc. Natl. Acad. Sci. USA, 87, 9020 (1990)]. Furthermore β-amyloid also facilitates neuronal deaths induced by excitatory amino acids such as glutamate and N-methyl-D-aspartate (NMDA) [Brain Res., 533, 315 (1990)]. As such, these facts may be able to account for the pathological findings related to β-amyloid in AD.

Recent findings have implicated that abnormalities in the astrocyte functions are found in AD patients. In addition, reactive astrocytes have been postulated to relate directly to AD induction [Neurol., 40, 33 (1990) Neurobiol. Aging, 13, 239 (1992)].

However, it is still unclear as to why reactive astrocytosis would occur superfluously. The present inventors therefore studied the inductions of reactive astrocytes so as to define the physiological functions of this endogenous element using primary cultured astrocytes from neonatal rat brains. By culturing astrocytes from physically destroyed brains by normal culture procedure, the reactive astrocytes were successfully induced. Consequently, in addition to a remarkably abnormal cell proliferation initiated on 5 days in vitro (DIV), enhanced glial fibrillary acidic protein (GFAP) contents and specific morphological changes (hyperplasia) in the reactive astrocytes were also observed.

After establishing and confirming the above findings, the functional changes which occurred during the induction of reactive astrocytes were pursued. The results did not revealed any significant changes in the voltage-dependent calcium, sodium and potassium channels and glutamate receptor responses in reactive astrocytes. However, a disappearance of GABA$_A$ receptor responses as inhibitory regulation was accompanied by the attenuated abnormal proliferation of astrocytes in cultures. The response decreased to such an extent that the astrocyte growth was rendered undetectable. Based on the observation that no receptor responses to glycine (an inhibitory amino acid) were elicited, reactive astrocytes were probably induced by a decrease in the inhibitory control of astrocytes.

All in all, when encephalopathy occurred, a disappearance of GABA$_A$ receptor responses of astrocytes ensued. Because astrocytes persisted abnormally, atypical levels of neurotransmitters and cytokines (especially NGF and β-APP) were released. These extraordinary events then produced synergistic effects that eventually induced abnormal ramifications/extension of neuronal dendrites followed by neuronal death. In other words, sideration of neurodegenerative diseases ensued.

Hence, treatment and/or prevention of neurodegenerative diseases attributed to functional abnormalities can be innovated and designed by improving the GABA$_A$ receptor responses of reactive astrocytes.

Furthermore, excessive glutamate and aspartate released at the terminals of ischemic neurons in brain insults cause persistent depolarization that eventually neutralizes the neurons concerned [Nikkei Sci. J., 9, 52 (1991)]. This event is then followed by excessive brain edema and encephalophyma (or astrocytosis), which in turn is ensued by death. As neurotoxic activities induced by the excessive response of reactive astrocytes are suppressed, GABA$_A$ receptor responses of astrocytes are improved. These events thus reduce not only the ischemia-induced mortality cases but can also alleviate/treat the post-ischemia brain dysfunction.

RELATED ARTS

Hitherto, drugs that improve a disappearance of GABA$_A$ receptor responses have not been discovered.

PURPOSE OF INVENTION

Based on findings on the excessive response of reactive astrocytes were induced by lack of inhibitory control ability of astrocytes, the present inventors attempted to improve the functional activities of such astrocytes by using various synthesized inhibitory compounds. As results, the present inventors have found that pentanoic acid derivative(s) were potentially useful in improving the GABA$_A$ receptor responses and have accomplished the present invention.

COMPARISON WITH THE RELATED ARTS

The compound of the present invention of the formula (I) and non-toxic salts thereof and acid addition salts thereof are all novel compounds.

In the compound of the formula (X), 2-propylpentanoic acid, 2-propylpentanamide, 2-propylhexanoic acid, 2-propylheptanoic acid, 2-propyloctanoic acid, 2-propylnonanoic acid, 2-propyldecanoic acid, 5-methyl-2-propylhexanoic acid, 2-cyclohexylpentanoic acid, methyl 2-cyclohexylpentanoate, ethyl 2-cyclohexylpentanoate, 2-(2-cyclohexylethyl)pentanoic acid, 2-(3-cyclohexylpropyl)pentanoic acid, 7-fluoro-2-propylheptanoic acid, 8-fluoro-2-propyloctanoic acid, 9-fluoro-2-propyinonanoic acid, 5,5,5-trifluoro-2-propylpentanoic acid, 2-chloro-2-propylpentanoic acid, 2-propyl-2-pentenoic acid, 2-propyl-3-pentenoic acid, 2-propyl-4-pentenoic acid, 2-ethylpentanoic acid and 2-ethylhexanoic acid are already known.

For example, 2-propylpentanoic-acid is known as valproic acid and 2-propylpentanamide is known as valpromide which already used as antiepileptic. 2-Propyl-2-pentenoic acid, 2-propyl-3-pentenoic acid and 2-propyl-4-pentenoic acid are known as metabolites of valproic acid and 2-ethylpentanoic acid, 2-ethylhexanoic acid and 2-propylhexanoic acid are known as analogues of valproric acid [Neuropharmacology, 24(5), 427–435(1985)]. 5,5,5-Trifluoro-2-propylpentanoic acid is disclosed as antiepileptic in Japanese Kokai Koho 6-116200. The following compounds are known in Chemical Abstracts Service, but they are not used as pharmaceuticals. Registry Number is described in parentheses.

2-propylheptanoic acid (31080-39-4),
2-propyloctanoic acid (31080-41-8),
2-propylnonanoic acid (65185-82-2),
2-propyldecanoic acid (123790-07-8),
5-methyl-2-propylhexanoic acid (94072-28-3),
2-cyclohexylpentanoic acid (106854-67-5),
methyl 2-cyclohexylpentanoate (102617-56-1),
ethyl 2-cyclohexylpentanoate (22579-21-1),
2-(2-cyclohexylethyl)pentanoic acid (28396-40-9),
2-(3-cyclohexylpropyl)pentanoic acid (15331-26-7),
7-fluoro-2-propylheptanoic acid (6863-43-0),
8-fluoro-2-propyloctanoic acid (3847-39-0),
9-fluoro-2-propylnonanoic acid (3847-35-6),
2-chloro-2-propylpentanoic acid (143100-15-6).

And 2-propyloctanoic acid and 2-propylnonanoic acid are already on the market as reagents.

Activities of valproic acid for astrocyte are known as follows until now.

(1) Inhibition of γ-aminobutylic-acid amino transferase (GABA-T) [Neuropharmacology, 25, 617-(1986)].

(2) Inducing of expression of glia heat shock protein as collagen type IV receptor [Brain Res., 459, 131 (1988)].

(3) Suppression of increase of glia [Brain Res., 554, 223 (1991)].

(4) Decreasing of affinity for taking in GABA [Neurochem. Res., 17, 327 (1992)].

Inhibition of inducing of reactive astrocyte which is discovered by the present inventors, is not known at all.

It is not able to expect at all that valproic acid has an inhibitory activity of inducing of reactive astrocyte from the above known activity. Further, it is the first discovery that the compounds of the formula (X), including 2-propylhexanoic acid, 2-propylheptanoic acid, 2-propyloctanoic acid, 2-propylnonanoic acid, 2-propyldecanoic acid, 5-methyl-2-propylhexanoic acid, 2-cyclohexylpentanoic acid, methyl 2-cyclohexylpentanoate, ethyl 2-cyclohexylpentanoate, 2-(2-cyclohexylethyl)pentanoic acid, 2-(3-cyclohexylpropyl)pentanoic acid, 7-fluoro-2-propylheptanoic acid, 8-fluoro-2-propyloctanoic acid, 9-fluoro-2-propylnonanoic acid, 5,5,5-trifluoro-2-propylpentanoic acid, 2-chloro-2-propylpentanoic acid and 2-propyl-2-pentenoic acid, have an inhibitory activity of inducing of reactive astrocyte.

DISCLOSURE OF THE INVENTION

The present invention is related to novel compounds, process for the preparation of the novel compounds, a use of the novel compounds and a novel use of known compounds.

Accordingly, the present invention is related to
1) the compound of the formula (I):

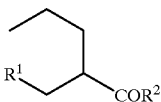

wherein $R^1$ is C1-10 alkyl having one carbon substituted by 1–3 of fluorine(s);
$R^2$ is hydroxy, C1-4 alkoxy, C1-4 alkoxy substituted by 1 of phenyl, or $NR^3R^4$,
in which $R^3$ and $R^4$ each, independently, is
(i) hydrogen,
(ii) C1-4 alkyl,
(iii) phenyl,
(iv) phenyl substituted by C1-4 alkoxy or carboxyl,
(v) 4-7 membered heterocyclic ring containing one nitrogen or
(vi) C1-4 alkyl substituted by phenyl, phenyl substituted by C1-4 alkoxy or carboxyl, or 4-7 membered heterocyclic ring containing one nitrogen, or the nitrogen atom bonded to them, taken together is 4–7 membered saturated heterocyclic ring containing one or two nitrogen(s) or one nitrogen and one oxygen, or amino acid residue;
with the proviso that, $R^1$ is not F—$(CH_2)_4$—, F—$(CH_2)_5$—, F—$(CH_2)_6$—, $F_3C$—$CH_2$—; and non-toxic salts thereof and acid addition salts thereof,
2) improving agent of the brain functions containing the compound of the formula (I), non-toxic salts thereof and acid addition salts thereof as active ingredient,
3) process for the preparation of the compound of the formula (I), non-toxic salts thereof and acid addition salts thereof,
4) improving agent of the brain functions containing the compound of the formula (X):

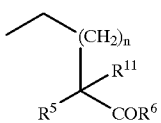

wherein n is 0 or 1;
$R^{11}$ is hydrogen or chlorine;
$R^5$ is $R^7$—$CH_2$— or $R^8$, or
$R^5$ and $R^{11}$, taken together is C3-10 alkylidene;
$R^7$ is F—$(CH_2)_m$—, in which m is 4–6,
$F_3C$—$CH_2$—, C2-10 alkyl substituted by 1 or 2 of chlorine (s), or C1-5 alkyl substituted by 1 or 2 of C1-4 alkoxy, C3-7 cycloalkyl, phenyl or phenoxy;
$R^8$ is (i) C3-10 alkyl
(ii) C3-10 alkenyl,
(iii) C2-10 alkoxy,
(iv) C2-10 alkylthio,
(v) C3-7 cycloalkyl,
(vi) phenyl or
(vii) phenoxy;
$R^6$ is hydroxy, C1-4 alkoxy, C1-4 alkoxy substituted by 1 of phenyl, or $NR^9R^{10}$,
in which $R^9$ and $R^{10}$ each, independently, is
(i) hydrogen,
(ii) C1-4 alkyl,
(iii) phenyl,
(iv) phenyl substituted by C1-4 alkoxy or carboxyl,
(v) 4-7 membered heterocyclic ring containing one nitrogen or
(vi) C1-4 alkyl substituted by phenyl, phenyl substituted by C1-4 alkoxy or carboxyl, or 4–7 membered heterocyclic ring containing one nitrogen, or the nitrogen atom bonded to them, taken together is 4–7 membered saturated heterocyclic ring containing one or two nitrogen(s) or one nitrogen and one oxygen, or amino acid residue; non-toxic salts thereof and acid addition salts thereof.

In the formula (I), C1-10 alkyl having one carbon substituent by 1–3 of fluoride(s) represented by $R^1$ means methyl, ethyl, propyl, butyl, pentyl, hexyl, heptyl, octyl, nonyl, decyl and isomeric groups thereof having one carbon substituted by 1, 2 or 3 of fluorine(s) and all groups are preferable. Especially preferable group is C1-7 alkyl having one carbon substituent by 1–3 of fluorine(s).

C1-4 alkoxy represented by $R^2$, $R^6$ or C1-4 alkoxy as a substituent of phenyl in $R^3$, $R^4$, $R^9$ or $R^{10}$ means methoxy, ethoxy, propoxy, butoxy and isomeric groups thereof and all groups are preferable. It's also preferable that $R^2$ or $R^6$ is hydroxyl.

C1-4 alkyl represented by $R^3$, $R^4$, $R^9$ or $R^{10}$ means methyl ethyl, propyl, butyl and isomeric groups thereof.

4–7 membered heterocyclic ring containing one nitrogen represented by $R^3$, $R^4$, $R^9$ or $R^{10}$ means pyrrole, pyridine, azepine or partially saturated rings thereof or all saturated rings (pyrrolidine, piperidine etc.) and all rings are preferable. Especially preferable ring is pyridine.

4–7 membered saturated heterocyclic ring containing one nitrogen represented by $R^3$, $R^4$ and the nitrogen atom bonded to them, or $R^9$, $R^{10}$ and nitrogen atom bonded to them means azetidine, pyrrolidine, piperidine or perhydroazepine and all rings are preferable. Especially preferable ring is piperidine.

4–7 membered saturated heterocyclic ring containing two nitrogens represented by $R^3$, $R^4$ and the nitrogen atom bonded to them, or $R^9$, $R^{10}$ and nitrogen atom bonded to them means pyrazolidine, imidazolidine, perhydrodiazine (piperazine etc.) perhydrodiazepine and all rings are preferable. Especially preferable ring is piperazine.

4–7 membered saturated heterocyclic ring containing one nitrogen and one oxygen represented by $R^3$, $R^4$ and the nitrogen atom bonded to them, or $R^9$, $R^{10}$ and nitrogen atom bonded to them means oxazolidine, perhydroxazine (morpholine etc.) perhydroxazepine and all rings are preferable. Especially preferable ring is morpholine.

The amino acid residue which is constituted by $R^3$, $R^4$ and the nitrogen atom bonded to them, or $R^9$, $R^{10}$ and nitrogen atom bonded to them means any amino acid residue. The amino acid residue may also includes the esters which is converted the carboxyl part of it. For example, they are glycine, alanine, serine, cysteine, cystine, threonine, valine, methionine, leucine, isoleucine, norleucine, phenylalanine, tyrosine, thyronine, proline, hydroxyproline, tryptophane, aspartic acid, glutamic acid, arginine, lysine, ornithine, histidine residue or ester (C1-4 alkyl ester or benzyl ester) thereof. Especially preferable amino acid is glycine.

C2-10 alkyl represented by $R^7$ means ethyl, propyl, butyl, pentyl, hexyl, heptyl, octyl, nonyl, decyl and isomeric groups thereof and C1-5 alkyl represented by $R^7$ means ethyl, propyl, butyl, pentyl and isomeric groups thereof.

C1-4 alkoxy as substituent of C1-5 alkyl in $R^7$ means methoxy, ethoxy, propoxy, butoxy and isomeric groups thereof. C3-7 cycloalkyl represented by $R^7$ means cyclopropyl, cyclobutyl, cyclopentyl, cyclohexyl and cycloheptyl.

C3-10 alkyl represented by $R^8$ means propyl, butyl, pentyl, hexyl, heptyl, octyl, nonyl, decyl and isomeric groups thereof and all groups are preferable. Especially preferable group is C3-7 alkyl.

C3-10 alkenyl represented by $R^8$ means propenyl, butenyl, pentenyl, hexenyl, heptenyl, octenyl, nonenyl, decenyl and isomeric groups thereof and all groups are preferable. C2-10 alkoxy means ethoxy, propoxy, butoxy, pentyloxy, hexyloxy, heptyloxy, octyloxy, nonyloxy, decyloxy and isomeric groups thereof and all groups are preferable. C2-10 alkylthio means ethylthio, propylthio, butylthio, pentylthio, hexylthio, heptylthio, octylthio, nonylthio, decylthio and isomeric groups thereof and all groups are preferable. C3-7 cycloalkyl means cyclopropyl, cyclobutyl, cyclopentyl, cyclohexyl and cycloheptyl and all groups are preferable.

C3-10 alkylidene represented by $R^5$ and $R^{11}$, taken together means propylidene, butylidene, pentylidene, hexylidene, heptylidene, octylidene, nonylidene, decylidene and isomeric groups thereof and all groups are preferable.

Preferable Compounds

In the compounds of the present invention of the formula (I), the compounds described in Example and the following compounds are preferable.

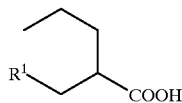

(1)

| $R^1$ |
| --- |
| $FH_2C—(CH_2)_6—$ |
| $FH_2C—(CH_2)_7—$ |
| $FH_2C—(CH_2)_8—$ |
| $FH_2C—(CH_2)_9—$ |
| $F_2HC—(CH_2)_6—$ |
| $F_2HC—(CH_2)_7—$ |
| $F_2HC—(CH_2)_8—$ |
| $F_2HC—(CH_2)_9—$ |
| $F_3C—(CH_2)_6—$ |
| $F_3C—(CH_2)_7—$ |
| $F_3C—(CH_2)_8—$ |
| $F_3C—(CH_2)_9—$ |

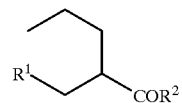

(2)

| $R^1$ | $R^2$ |
| --- | --- |
| $FH_2C—(CH_2)_2—$ | $—NH_2$ |
| " | $—NHC_2H_5$ |
| " | $—N(CH_3)_2$ |
| " | 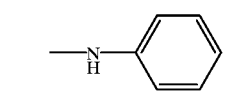 |
| " | 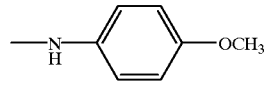 |
| " | 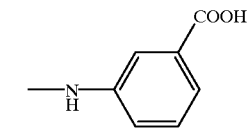 |

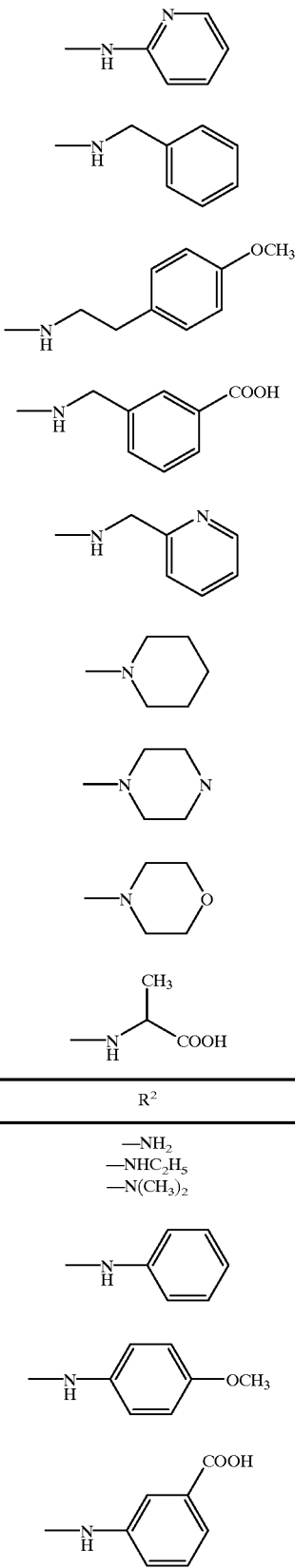

| $R^1$ | $R^2$ |
| --- | --- |
| $F_2HC—(CH_2)_4—$ | $—NH_2$ |
| " | $—NHC_2H_5$ |
| " | $—N(CH_3)_2$ |

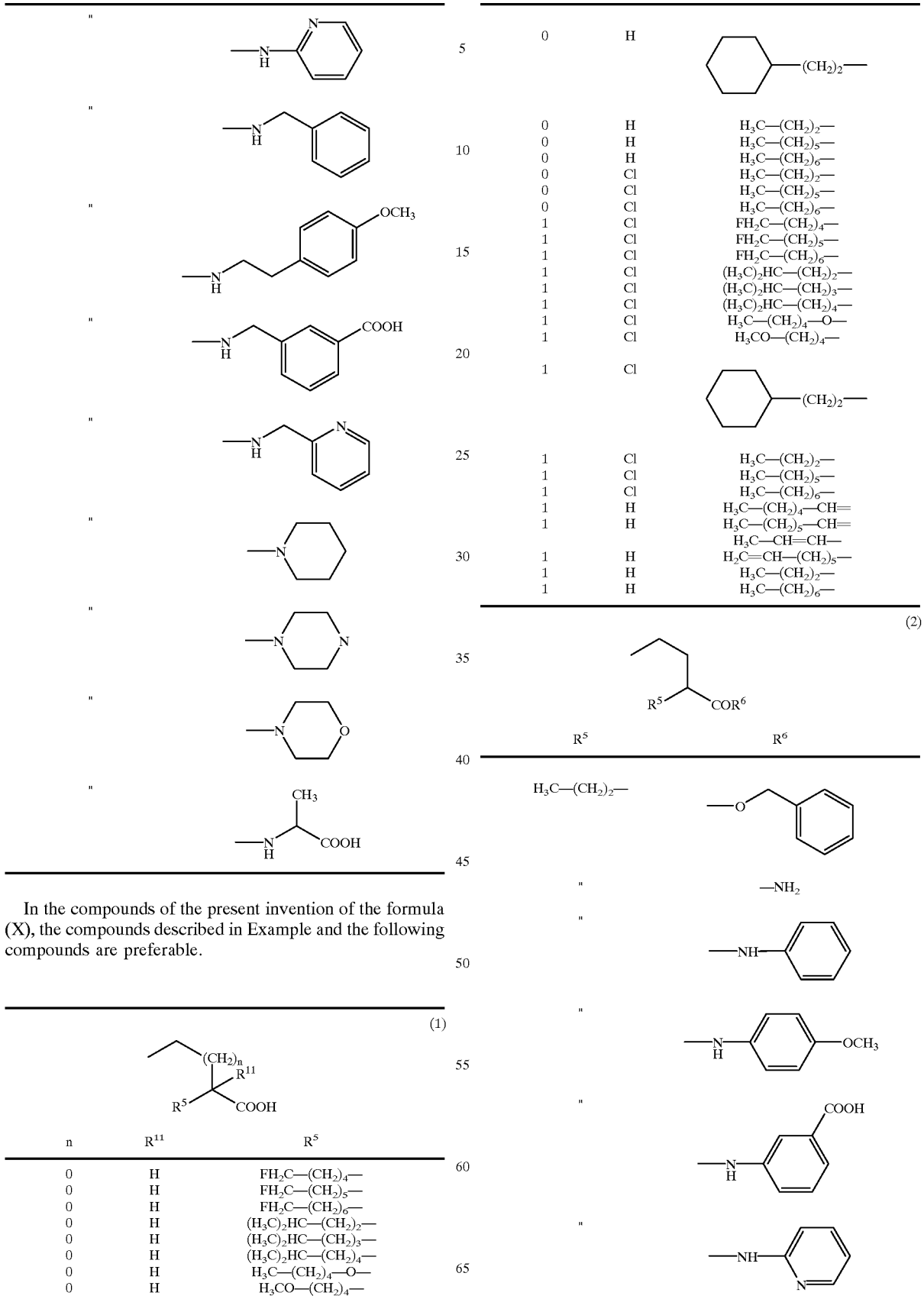
In the compounds of the present invention of the formula (X), the compounds described in Example and the following compounds are preferable.

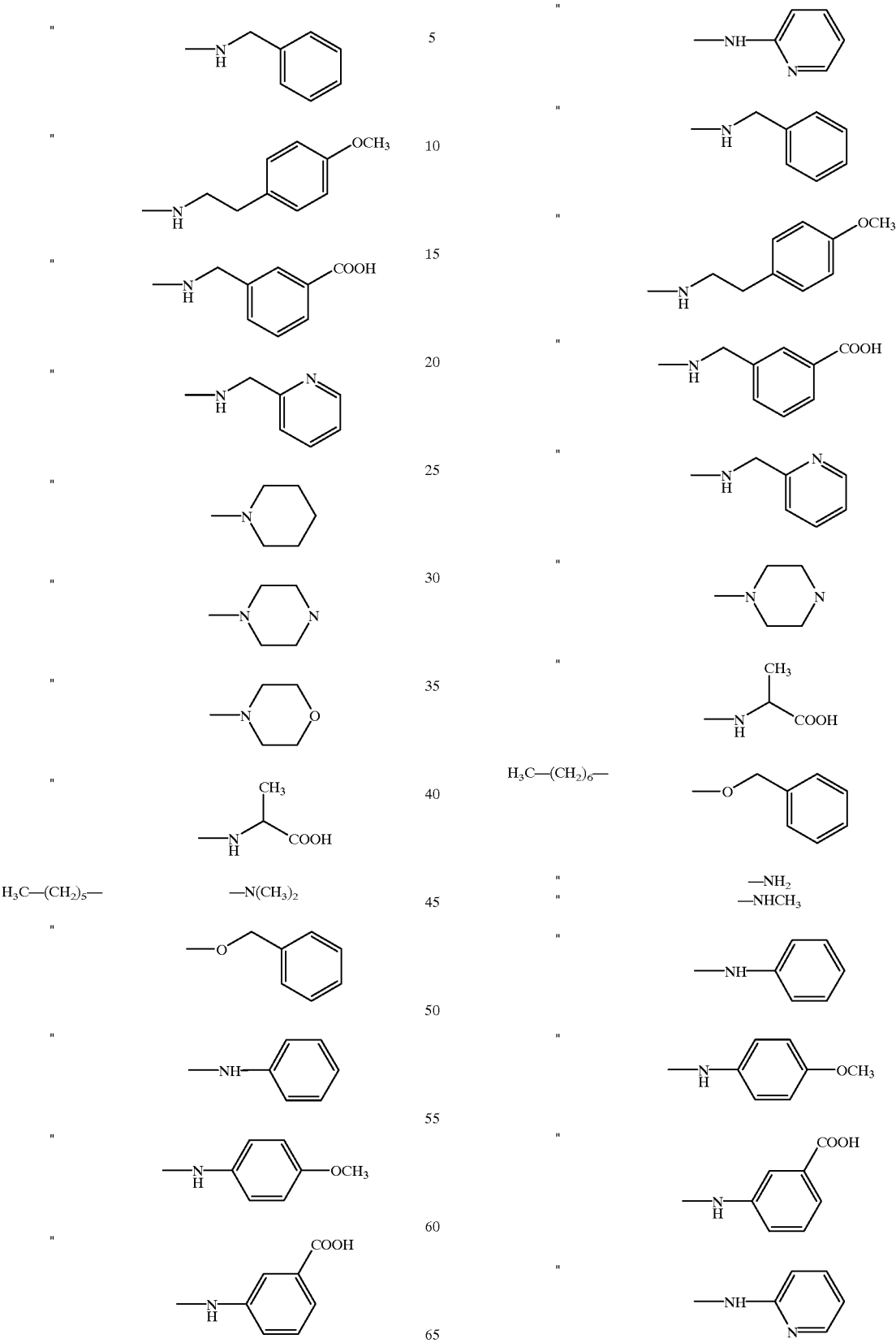

-continued

| | | |
|---|---|---|
| " | –NH–CH₂–C₆H₅ (N-benzyl) | |
| " | –NH–CH₂CH₂–C₆H₄–OCH₃ (4-methoxy) | |
| " | –NH–CH₂–C₆H₄–COOH (3-carboxy) | |
| " | –NH–CH₂–(2-pyridyl) | |
| " | N-methylpiperidine | |
| " | N-methylpiperazine | |
| " | N-methylmorpholine | |
| " | –NH–CH(CH₃)–COOH | |
| FH₂C—(CH₂)₄— | –O–CH₂–C₆H₅ | |
| " | –NH₂ | |
| " | –NHCH₃ | |
| " | –NH–C₆H₅ | |
| " | –NH–C₆H₄–OCH₃ (4-methoxy) | |
| " | –NH–C₆H₄–COOH (3-carboxy) | |

-continued

| | | |
|---|---|---|
| " | –NH–(2-pyridyl) | |
| " | –NH–CH₂–C₆H₅ | |
| " | –NH–CH₂CH₂–C₆H₄–OCH₃ (4-methoxy) | |
| " | –NH–CH₂–C₆H₄–COOH (3-carboxy) | |
| " | –NH–CH₂–(2-pyridyl) | |
| " | N-methylpiperidine | |
| " | N-methylpiperazine | |
| " | N-methylmorpholine | |
| " | –NH–CH(CH₃)–COOH | |
| FH₂C—(CH₂)₆— | –O–CH₂–C₆H₅ | |
| " | –NH₂ | |
| " | –NHCH₃ | |
| " | –NH–C₆H₅ | |
| " | –NH–C₆H₄–OCH₃ (4-methoxy) | |

In the present invention, it is able to formulate using each active ingredient or combination of more than two active ingredients.

Unless otherwise specified, all isomers are included in the invention. For example, alkyl, alkoxy and alkenyl includes straight and branched ones. Double bond in alkenyl includes E, Z and EZ mixture. Isomers generated by 23 (, asymmetric carbon(s) e.g. branched alkyl are included in the present invention.

Salts

The compounds which $R^2$ is hydroxyl among the compounds of the formula (I) or $R^6$ is hydroxyl among the compounds of the formula (X), of the present invention may be converted into the corresponding salts. Non-toxic and water-soluble salts are preferable. Suitable salts, for example, are as follows:

salts of alkaline metal (sodium, potassium etc.), salts of alkaline earth metal (calcium, magnesium etc.), ammonium salts, salts of pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

Acid addition salts The compounds of the formula (I) and (X) may be converted into the corresponding acid addition salts. Non-toxic and water-soluble salts are preferable. Suitable salts, for example, are as follows:

salts of inorganic acids e. g. hydrochloride, hydrobromide, hydroiode, sulfate, phosphate, nitrate; salts of organic acids e. g. acetate, lactate, tartarate, benzoate, citrate, methanesulphonate, ethanesulphonate, benzenesulphonate, toluenesulphonate, isedthioate, glucuronate, gluconate.

Process for the preparation

The compounds of the present invention of the formula (I), may be prepared:

(i) by subjecting a compound of the formula (II):

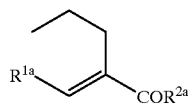

(II)

wherein $R^{1a}$ is C1-10 alkyl having one carbon substituted by 1 or 2 of fluorine(s) and $R^{2a}$ is C1-4 alkoxy;

or the compound of the formula (V):

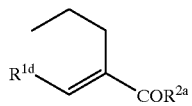

(V)

wherein $R^{1d}$ is C1-10 alkyl having one carbon substituted by 3 of fluorines and $R^{2a}$ is the same meaning as hereinbefore defined;

or the compound of the formula (VIII):

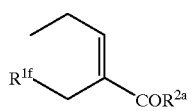

(VIII)

wherein $R^{1f}$ is C1-10 alkyl having one carbon substituted by 3 of fluorines and $R^{2a}$ is the same meaning as hereinbefore defined; to hydrogenation, (ii) by hydrolysis of ester in an alkaline condition of the compound of the formula (I-a):

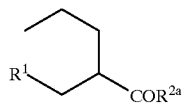

(I-a)

wherein all the symbols are the same meaning as hereinbefore defined, (iii) by reacting of the acyl chloride compound of the formula (I-b):

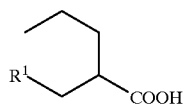

(I-b)

wherein $R^1$ is the same meaning as hereinbefore defined;

(iii-1) with a compound of the formula (A):

$HNR^3R^4$ (A)

wherein $R^3$ and $R^4$ are the same meaning as hereinbefore defined; or (iii-2) with a compound of the formula (H):

$R^{2b}$—OH (H)

wherein $R^{2b}$ is C1-4 alkyl substituted by 1 of phenyl.

And the compound which $NR^3R^4$ is the amino acid residue containing unesterfied carboxyl group in the formula (I), may be prepared by subjecting the compound which $NR^3R^4$ is the amino acid wherein carboxyl group is esterfied by benzyl in the formula (I-C):

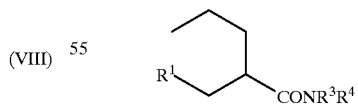

(I-c)

wherein all symbols are the same meaning as hereinbefore defined; obtained by reaction (iii-1), to hydrogenation.

The compounds of the formula (II), (V), (VIII), (I-a) and (I-b) may be prepared by using a reaction depicted in following Scheme (A-1) and (A-2).

Scheme (A-1)

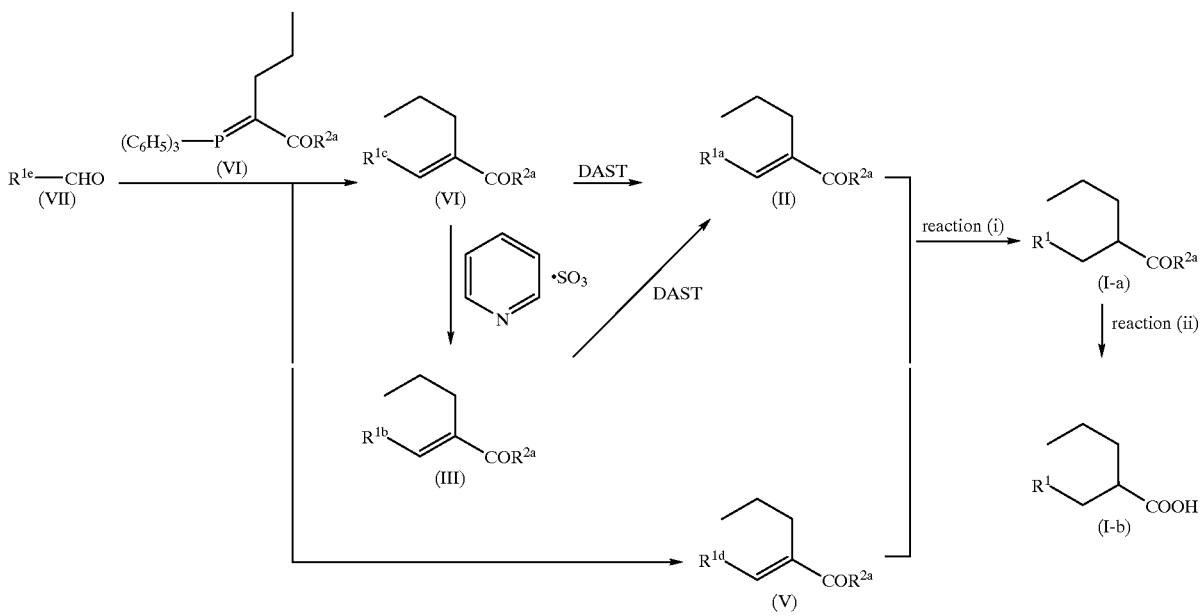

Scheme (A-2)

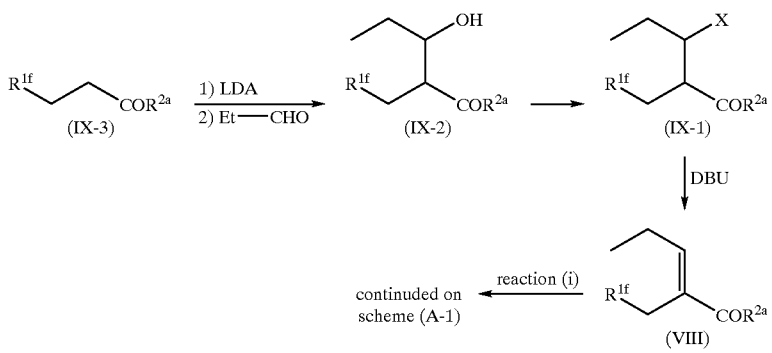

In the scheme, $R^{1b}$ is C1-10 alkyl having one carbon substituted by one ketone, $R^{1c}$ is C1-10 alkyl having one carbon substituted by one hydroxyl, $R^{1e}$ is C1-10 alkyl having one carbon substituted by one hydroxyl or three fluorines, X is mesylate, tosylate or halogen atoms, and the other symbols are the same meaning as hereinbefore defined. DAST is diethylaminosulfure trifluoride, LDA is lithium diisopropylamide, DBU is 1,8-diazabicyclo[5.4.0]undec-7-ene.

The hydrogenation of the reaction (i) is known, for example, it may be carried out in an organic solvent (tetrahydrofuran (THF), dioxane, diethylether, ethyl acetate, methanol, ethanol, etc.) using a catalyst (palladium on carbon, palladium, hydroxy palladium, palladium acetic acid, palladium black, platinum black, nickel, Ranney nickel, etc.) at normal or elevated pressure of hydrogen gas, at 0–80° C.

The hydrolysis of ester in an alkaline condition of the reaction (ii) is known, for example, it may be carried out in water miscible organic solvent (THF, dioxane, ethanol, methanol, dimethoxyethane or two or more of the mixture, etc.) using an aqueous solution of an alkaline (potassium hydroxide, sodium hydroxide, etc.) at –10–100° C.

The amidation of the reaction (iii-1) is known, for example, it may be carried out with oxalyl chloride, and then by reacting a compound thus obtained with an amine of the formula $NR^3R^4$, wherein $R^3$ and $R^4$ are the same meaning as hereinbefore defined, in an inert organic solvent (THF, methylene chloride, toluene, diethylether, etc.), in the presence or absence of an appropriate base (triethylamine, etc.) at 0–40° C.

And, the hydrogenation is the same process as hereinbefore defined.

The reaction (iii-2) is known, for example, it may be carried out with oxalyl chloride, and then by-reacting a compound thus obtained with an alcohol of the formula $R^{2b}$—OH, wherein $R^{2b}$ is the same meaning as hereinbefore defined, in an inert organic solvent (THF, methylene chloride, toluene, diethylether, etc.), in the presence or absence of an appropriate base (triethylamine, etc.) at 0–40° C.

The compounds of the formula (X) in the present invention, may be prepared:

(i) by subjecting a compound of the formula (XI):

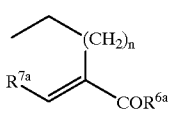

(XI)

wherein $R^{7a}$ is F—$(CH_2)_m$—, in which m is 4–6, $R^{6a}$ is C1-4 alkoxy and n is the same meaning as hereinbefore defined; or the compound of the formula (XIII):

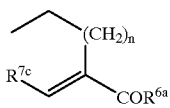

(XIII)

wherein $R^{7c}$ is $F_3C$—$CH_2$—, C2-10 alkyl substituted by 1 or 2 of chlorine(s), or C1-5 alkyl substituted by 1 or 2 of C1-4 alkyl, C3-7 cycloalkyl, phenyl or phenoxy, and $R^{6a}$ and n are the same meaning as hereinbefore defined; to hydrogenation, (ii) by subjecting a compound of the formula (XVI):

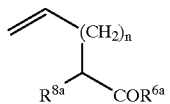

(XVI)

wherein $R^{8a}$ is C3-10 alkyl and the other symbols are the same meaning as hereinbefore defined; to hydrogenation, (iii) by reacting a compound of the formula (XVIII):

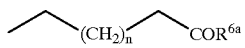

(XVIII)

wherein all the symbols are the same meaning as hereinbefore defined;
with the formula (D):

$R^{8b}$—Br (D)

wherein $R^{8b}$ is C3-10 alkenyl; or
with the formula (E):

$(R^{8c}$—$S)_2$ (E)

wherein $R^{8c}$ is C2-10 alkyl, (iv) by reacting a compound of the formula (XIX):

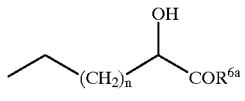

(XIX)

wherein all the symbols are the same meaning as hereinbefore defined; with the formula (F):

$R^{8d}$—I (F)

wherein $R^{8d}$ is C2-10 alkyl, (v) by reacting a compound of the formula (XX):

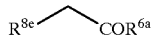

(XX)

wherein $R^{8e}$ is phenyl, phenoxy or C3-7 cycloalkyl and $R^{6a}$ is the same meaning as hereinbefore defined;
with the formula (G):

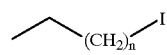

(G)

wherein n is the same meaning as hereinbefore defined;

(vi) by subjecting a compound of the formula (XXI):

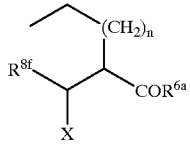

(XXI)

wherein $R^{8f}$ is C2-9 alkyl, X is mesylate, tosylate or halogen atoms and R6a and n are the same meaning as hereinbefore defined; to elimination reaction, (vii) by reacting a compound of the formula (X-a):

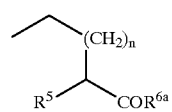

(X-a)

wherein all the symbols are the same meaning as hereinbefore defined;
with carbon tetrachloride, (viii) by subjecting a compound of the formula (X-d):

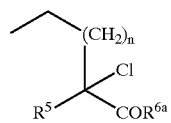

(X-d)

wherein all the symbols are the same meaning as hereinbefore defined; to reduction reaction and oxidation reaction, (ix) by hydrolysis of ester in an alkaline condition of the compound of the formula (X-a):

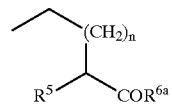

(X-a)

wherein all the symbols are the same meaning as hereinbefore defined;

(x) by reacting of the acyl chloride compound of the formula (X-b):

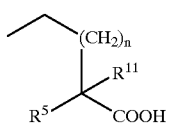
(X-b)

wherein all the symbols are the same meaning as hereinbefore defined;

(x-1) with a compound of the formula (B):

HNR$^9$R$^{10}$ (B)

wherein R$^9$ and R$^{10}$ are the same meaning as hereinbefore defined; or (x-2) with a compound of the formula (J):

R$^{6b}$—OH (J)

wherein R$^{6b}$ is C1-4 alkyl substituted by 1 of phenyl.

And the compound which NR$^9$R$^{10}$ is the amino acid residue containing unesterfied carboxyl group in the formula (X), may be prepared by subjecting the compound which NR$^9$R$^{10}$ is the amino acid wherein carboxyl group is esterfied by benzyl in the formula (X-C):

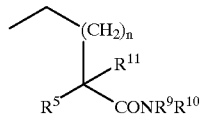
(X-c)

wherein all the symbols are the same meaning as hereinbefore defined;

obtained by reaction (x-1), to hydrogenation.

The compounds of the formula (XI), (XIII), (XVI), (XXI), (X-a), (X-b) and (X-d) may be prepared by using a reaction depicted in following Scheme (B-1), (B-2) and (B-3).

Scheme (B-1)

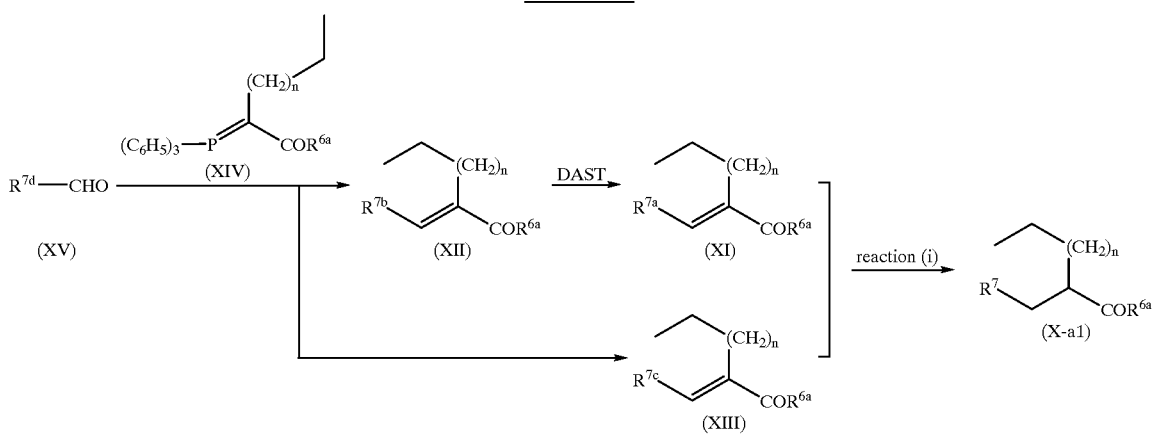

Scheme (B-2)

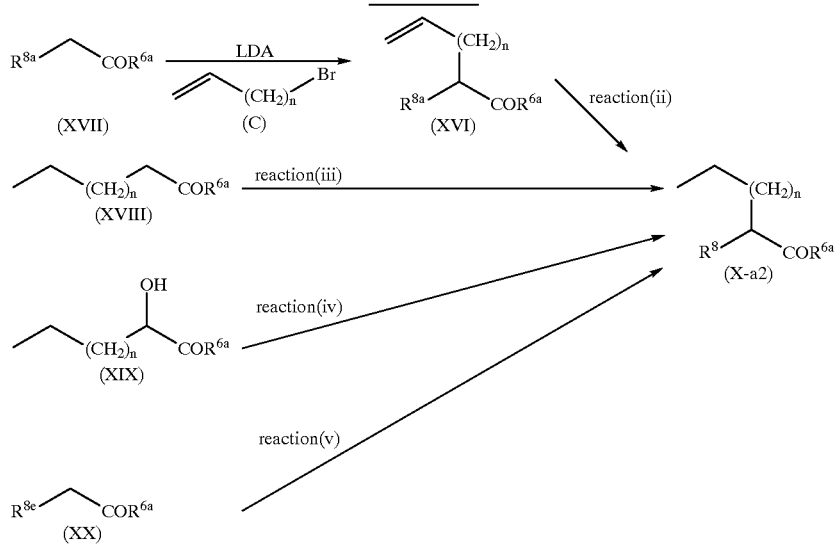

Scheme (B-3)

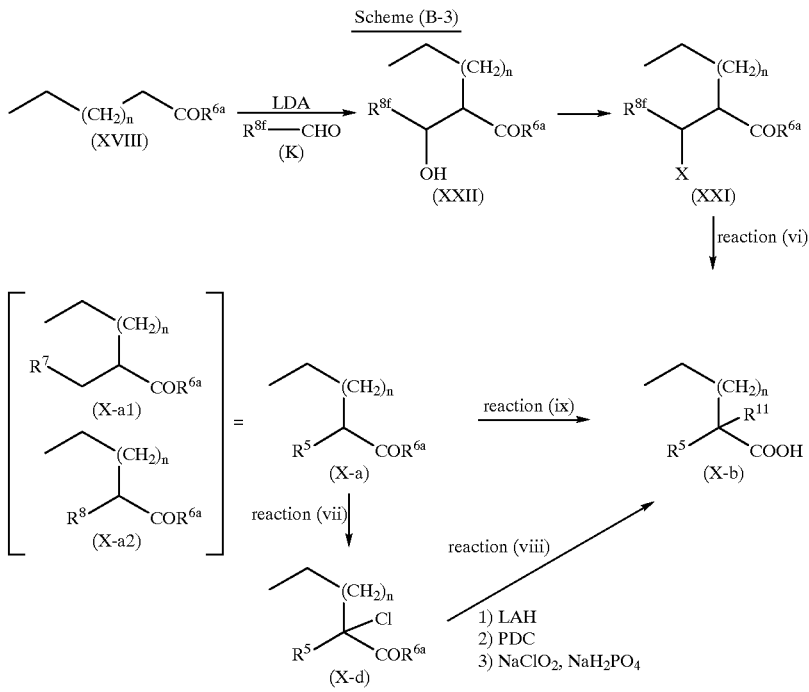

In the scheme, $R^{7b}$ is HO—$(CH_2)_n$—, wherein n is the same meaning as hereinbefore defined, $R^{7d}$ is HO—$(CH_2)_n$—, wherein n is the same meaning as hereinbefore defined, or $F_3C$—$CH_2$—, or C2-10 alkyl substituted by 1 or 2 of chlorine(s), or C1-5 alkyl substituted by 1 or 2 of C1-4 alkoxy, C3-7 cycloalkyl, phenyl or phenoxy, and the other symbols are the same meaning as hereinbefore defined. DAST and LDA are the same meaning as hereinbefore defined, LAH is lithium aluminum hydride, PDC is pyridinium dichromate.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Starting materials and reagents

The starting materials and reagents in the present invention are known per se or may be prepared by known methods.

For example, the compound of the formula:

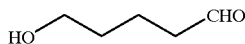

in the compounds of the formula (VII) is on the market.
The compound of the formula,

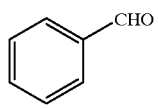

in the compounds of the formula (XV) is on the market.

The compound of the formula:

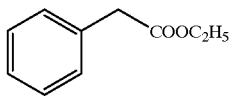

in the compounds of the formula (XX) is on the market.
The compound of the formula:

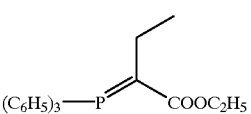

in the compounds of the formula (VI) may be prepared by known methods, for example, using the compound of the formula:

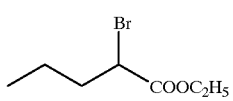

being on the market and triphenylphosphine being on the market.

And process of the preparation of 2-propylpentanoic acid and non-toxic salts thereof are described in specification of the U.S. Pat. No. 4,127,604.

Pharmacological Activities

The compounds of the present invention of the formula (I), the compounds of the formula (X), non-toxic salts thereof and acid addition salts are useful for improvement of cerebral function, for in animals including human beings, especially human beings, because they have an activity of functional improvement of astrocyte and their toxicity is very low. An object disease, for example are as follows:

Neurodegenerative disease (e.g. Alzheimer's disease, Amyotrophic lateral sclerosis, Progressive supra nuclear palsy, Olive-ponto-cerebellar atrophy), Neuronal dysfunction by stroke or traumic injury (e.g. Demyelinative disease (Multiple sclerosis etc.), Brain tumors (Astrocytoma etc.), Infection (Meningitis, Brain abscess, Creutzfeldt-Jakob disease, AIDS dementiaetc)).

For example, in standard laboratory test, the effects were confirmed as follows.

Experiment 1:
Effects in improving astrocyte functions
[Methods]

Preparation of astrocyte cultures:

After removing the meninges, isolated cerebrum of neonatal rats (age: day 1) were placed on frosted glass-slides and minced. The sample was then digested with trypsin (0.25%) and DNase 1 (0.02%) and suspended in 10% FCS-DMEM before centrifugation. After resuspending in 10%FCS-DMEM, the suspension was dispersed in dishes and cultured at 37° C. under 5% $CO_2$ atmosphere. Non-adherent cells were removed from the dishes after agitation/washing on post-culture 24 hours. Note that the adherent cell population was composed of more than 95% of GFAP-positive cells.

GFAP contents and $GABA_A$ receptor responses: The improvement effects on astrocyte functions were evaluated from the following indices: inhibition derived from the increase in GFAP content and inhibition in the disappearance of $GABA_A$ receptor responses. Thus, sodium valproate (Sigma Chem. Co., U.S.A.) was added on 1 DIV followed by whole-cell mode voltage-clamp method on 7 DIV-to measure the GABA ($3\times10^{-5}$ M)-induced Cl$^-$ current. The Cl$^-$ current was taken as an index for the GABA response. Furthermore, GFAP contents were determined by the ELISA method on 11 DIV.

[Results]

The results are shown in the Table 1. The GFAP contents were expressed as a ratio of the control group.

TABLE 1

The improvement effects on astrocyte functions

| Compound | Concentration (mM) | Ratio of increase in GFAP contents (%) | $GABA_A$ receptor responses (pA; means ± S.E.) |
|---|---|---|---|
| control | | 100.0 | 90 ± 43 |
| VPA* | 0.3 | 30.6 | 254 ± 106 |
| | 1.0 | 36.3 | 432 ± 98 |
| | 3.0 | 44.3 | 1301 ± 156 |

*VPA: sodium valproate

From Table 1, sodium valproate reversed the decreases in the $GABA_A$ receptor response, and the GFAP contents (index for reactive astrocytes) were remarkably suppressed.

Based on these findings, sodium valproate elicited potent effects in improving the astrocyte functions.

Experiment 2:
Regeneration effects of $GABA_A$ receptor responses against reactive astrocytes.
[Methods]

Astrocytes were prepared and cultured in a manner similar to Experiment 1. On 14 DIV, reactive astrocytes were subjected to a serial passage ($10^5$ cells/dish). The thus adherent reactive astrocytes were washed, and transferred to culture media containing the present effectively developed compound(s) or invention. On 14 DIV after serial passages, $GABA_A$ receptor responses were tested according to procedures designated in Experiment 1.

[Results]

The results are shown in Table 2 and 3.

TABLE 2

| Ex. No. | Concentration (mM) | $GABA_A$ receptor responses (pA; means ± S.E.) |
|---|---|---|
| control | | 8 ± 6 |
| 2 | 0.3 | 193 ± 103 |
| | 1.0 | 628 ± 227 |
| 2(2) | 0.1 | 114 ± 81 |
| | 0.3 | 527 ± 201 |
| 2(5) | 3.0 | 326 ± 148 |
| 2(6) | 0.3 | 184.0 ± 118.1 |
| | 3.0 | 528.0 ± 160.2 |
| 2(8) | 1.0 | 470.6 ± 124.9 |
| | 3.0 | 808.6 ± 325.4 |
| 2(9) | 0.3 | 236.4 ± 85.5 |
| 2(10) | 0.3 | 800.0 ± 415.6 |
| 2(12) | 1.0 | 672 ± 242 |
| | 3.0 | 1109 ± 227 |

TABLE 3

| Ex. No. | Concentration (mM) | $GABA_A$ receptor responses (pA; means ± S.E.) |
|---|---|---|
| control | | 8 ± 6 |
| VPA* | 0.3 | 37 ± 26 |
| | 1.0 | 193 ± 141 |
| | 3.0 | 1263 ± 303 |
| 7 | 0.3 | 213.1 ± 150.1 |
| | 1.0 | 661.7 ± 306.3 |
| 7(1) | 0.3 | 260.0 ± 47.3 |
| 7(2) | 0.3 | 730.0 ± 226.4 |
| 7(4) | 0.3 | 163.0 ± 60.4 |
| 7(8) | 1.0 | 59.0 ± 20.6 |
| 7(9) | 0.3 | 512.1 ± 233.1 |
| | 3.0 | 226.3 ± 60.5 |
| 7(14) | 3.0 | 285.7 ± 103.6 |
| 7(16) | 0.3 | 105 ± 65 |
| | 1.0 | 417 ± 140 |
| 7(17) | 0.3 | 259.0 ± 83.7 |
| 7(18) | 1.0 | 658.6 ± 440.7 |
| 7(26) | 3.0 | 344.7 ± 342.5 |
| 7(28) | 3.0 | 122 ± 44 |
| 7(30) | 0.3 | 233 ± 90 |
| | 1.0 | 675 ± 201 |
| 7(31) | 0.3 | 51 ± 28 |
| | 1.0 | 565 ± 278 |
| | 3.0 | 590 ± 180 |
| 7(32) | 0.1 | 48 ± 20 |
| 7(33) | 0.03 | 40 ± 23 |
| | 0.1 | 237 ± 69 |
| | 0.3 | 1260 ± 521 |
| 7(37) | 0.3 | 139 ± 52 |
| | 3.0 | 595 ± 190 |
| 9 | 3.0 | 467 ± 187 |
| 11 | 0.3 | 35 ± 15 |
| | 1.0 | 190 ± 134 |
| | 3.0 | 281 ± 174 |
| 13 | 3.0 | 171 ± 55 |
| 2-PNA** | 0.03 | 85 ± 41 |
| | 0.1 | 107 ± 50 |
| | 0.3 | 380 ± 124 |

*VPA: sodium valproate
**2-PNA: 2-propylnonanic acid

From Table 2 and 3, each active ingredient elicited marked regeneration effects on the loss of $GABA_A$ receptor responses. This finding indicated that the relevant compounds under investigation were effective in transforming reactive astrocytes to astrocytes.

Experiment 3:
Suppressive effects on-cell death in the symbiotic neurons-astrocytes co-culture system.
[Methods]
Astrocytes, prepared in a manner similar to that of Experiment 1, were cultured for 14 days. Previously prepared neurons ($3 \times 10^4$ cells/well), isolated from cerebrum of 19-day old fetus rats, were added to the cultured astrocytes ($3 \times 10^5$ cells/well) and allowed to grow. During the culture process, survival rates and neuronal dendrite extension/ramification of neurons were observed. Note that, sodium valproate (3 mM) and astrocytes were initially added to the neurons concomitantly, and freshly prepared similar culture media containing the invented compound (3 mM) were subsequently added at 3~4-day intervals.
[Results]
The results are shown in Table 4.

TABLE 4

Suppressive effects on neuron death

| Compound | Survival rates (on 22 days) |
|---|---|
| control | <10% |
| VPA | 60–70% |

VPA: sodium valproate

Almost all neurons in the control group died out, and dendrite generation was not observed. However, marked survival rates and dendrite generation in the neurons were detected in the sodium valproate-treated cultures.
Experiment 4:
Effects on experimental brain ischemia
[Methods]
Establishing the experimental brain ischemia model: Vertebral arteries of pentobarbital-anesthetized rats were bilaterally coagulated, and a period of 7 days was allowed for recovery. The previously surgically exposed bilateral common carotid arteries of ischemic rats were mechanically ligated for 20 min. Immediately after deligation, the rats were once daily injected i.p. with sodium valproate (300 mg/kg) for 4 consecutive days. On deligation day 5~6, mobility aspects in the conditional avoidance experiment were monitored.
Mobility aspects of the conditional avoidance experiment: The step-up model of the dark/light box was used. Animals placed in the dark section of the grid-floored box with the connecting door closed were allowed to accustomed to the environment for 1 minute. The door was then opened for 10 seconds. Rats that stepped up to the lighted section via the opened door were considered positive in the conditional avoidance test. Animals categorized as negative in the test were placed in the dark section with the door closed for 10 seconds prior to subjecting them to electric foot shock at 2 mA for 50 seconds. Those rats that did not mobilize to the lighted section of the box by the electric shock were omitted from the test. The above procedure was repeated 5 trials per day at 30-minutes intervals. A total of 10 trials within 2 days were attempted.
[Results]
The data are illustrated in FIG. 1. Compared to the ischemic reference group (2.8±0.8), the normal and sham-operated groups scored frequencies of 6.1±0.7 and 4.8±0.8, respectively. However, a count of 5.3±0.8 was registered in the sodium valproate-treated group, clarifying that mobility impairment of the learned conditional avoidance response induced by recirculation of the ischemic brain was improved by the invented compound(s).

Toxicity
The toxicity of each active ingredient in the present invention and non-toxic salts thereof and acid addition salts thereof are very low. For example, the acute toxicity ($LD_{50}$) in mouse of sodium valproate was 1700 mg/kg by oral administration (Merck Index, 11, pp1559). Therefore, each active ingredient in the present invention may be estimated to safe for pharmaceutical use.
Application for Pharmaceuticals
The compounds of the present invention of the formula (I) and the compounds of the formula (X), non-toxic salts thereof and acid addition salts thereof, are useful for improvement of cerebral function, because they have an activity of functional improvement of astrocyte.

For example, they are expected to be useful for neurodegenerarive disease (e.g. Alzheimer's disease, Amyotrophic lateral sclerosis, Progressive supra nuclear palsy, Olive-ponto-cerebellar atrophy), neuronal dysfunction by stroke or traumic injury, Demyelinative disease (Multiple sclerosis etc.), Brain tumors (Astrocytoma etc.), Infection (Meningitis, Brain abscess, Creutzfeldt-Jakob disease, AIDS dementia etc.).

For the purpose above described, each active ingredient in the present invention, non-toxic salts thereof and acid addition salts thereof may be normally administered systemically or partially, usually by oral or parenteral administration.

The doses to-be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 100 μg and 100 mg, by parenteral administration (preferable intravenous administration), up to several times per day.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.).

The compositions may also comprise, as is normal practice, additional substances other than inert diluents: e.g. lubricating agents (such as magnesium stearate etc.), disintegrating agents (such as cellulose calcium glycolate, etc.), stabilizing agents, and assisting agents for dissolving such as glutamic acid, etc.).

The tablets or pills may, if desired, be coated with a film of gastric or enteric material (such as sugar, gelatin, hydroxypropyl cellulose or hydroxypropylmethyl cellulose phthalate, etc.), or be coated with more than two films. And further, coating may include containment within capsules of absorbable materials such as gelatin.

Capsules include hard capsules and soft capsules.

Liquid compositions for oral administration include pharmaceutically-acceptable emulsions, solutions, syrups and elixirs. In such compositions, one or more of the active compound(s) is or are contained in inert diluent(s) commonly used in the art (Purified water, ethanol etc.).

Besides inert diluents, such compositions may also comprise adjuvants (such as wetting agents, suspending agents, etc.), sweetening agents, flavouring agents, perfuming agents, and preserving agents.

Other compositions for oral administration included spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. Aqueous solutions, suspensions include distilled water for injection and physiological salt solution. Non-aqueous solutions, suspensions include propylene glycol, polyethylene glycol, vegetable oil such as olive oil, alcohol such as ethanol, POLYSORBATE80 (registered trade mark), etc.

Injections may comprise additional other than inert diluents: e.g. preserving agents, wetting agents, emulsifying agents, dispersing agents, stabilizing agent (human serium albumin, lactose), assisting agents such as assisting agents for dissolving (arginine, glutamic acid, asparaginic acid, polyvinylpyrolydone etc.).

They may be sterilized for example, by filtration through a bacteria-retaining filter, by incorporation of sterilizing agents in the compositions or by irradiation. They may also be manufactured in the form of sterile solid compositions by freeze-drying and which may be dissolved in sterile water or some other sterile diluent(s) for injection immediately before used.

Other compositions for parenteral administration include liquids for external use, and endermic liniments, ointment, suppositories for rectal administration and pessaries for vaginal administration which comprise one or more of the active compound(s) and may be prepared by per se known methods.

REFERENCE EXAMPLES AND EXAMPLES

The following reference examples and examples illustrate the present invention, but not limit the present invention.

The solvents in the parentheses show the developing or eluting solvents and the rations of the solvents used are by volume in chromatographic separations.

Unless otherwise specified, "NMR" was measured in a methanol-d ($CD_3OD$) solution and "IR" was measured by the liquid film method respectively.

Reference example 1

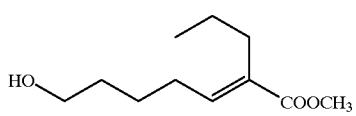

(1-Methoxycarbonyl-1-butylidene)triphenylphosphorane (5.52 g) was added to a solution of 5-hydroxypentanal (1.00 g) in benzene (15 ml) under an atmosphere of argon. The mixture was stirred for 15 hours at 80° C. The reaction mixture was concentrated under reduced pressure. The residue was purified by column on silica gel (hexane:ethyl acetate=3:1) to give the title compound (1.17 g) having the following physical data.

TLC: Rf 0.42 (hexane:ethyl acetate=2:1).

Reference example 2

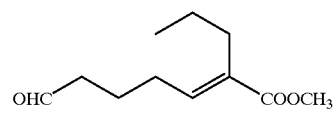

To a solution of the compound obtained in reference example 1 (389 mg) in tetrahydrofuran (5 ml), dimethylsulfoxide (5 ml), triethylamine (3 ml) and sulfur trioxide pyridine complex (619 mg), successively, were added under an atmosphere of argon. The mixture was stirred for 40 minutes at room temperature. The reaction solution was diluted with ether, washed with a saturated aqueous solution of ammonium chloride, water and a saturated aqueous solution of sodium chloride, successively, dried over anhydrous magnesium sulfate and concentrated under reduced pressure. The residue was purified by column on silica gel (hexane:ethyl acetate=7:1) to give the title compound (268 mg) having the following physical data.

TLC: Rf 0.55 (hexane:ethyl acetate=3:1).

Reference example 3

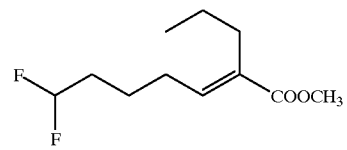

A solution of the compound obtained in reference example 2 (268 mg) in anhydrous dichloromethane (2 ml) was dropped to a solution of diethylaminosulfur trifluoride (DAST) (393 μl) in anhydrous dichloromethane (2 ml) under an atmosphere of argon at −78° C. The mixture was stirred for 2.5 hours at 0° C. The reaction mixture was diluted with ether, washed with water and a saturated aqueous solution of sodium chloride, successively, dried over anhydrous magnesium sulfate and concentrated under reduced pressure. The residue was purified by column on silica gel (hexane:ethyl acetate=20:1) to give the title compound (275 mg) having the following physical data.

TLC: Rf 0.49 (hexane:ethyl acetate=10:1).

Reference example 5

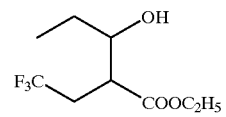

Tetrahydrofuran (THF) (6 ml) was cooled at −78° C. Lithium diisopropylamide (LDA) (2.94 ml) was added to the above THF, and stirred. Ethyl 4,4,4-trifluorobutanoate (1.00 g) was added to the mixture, and stirred for 20 minutes at −78° C. Propanal (0.47 ml) was dropped to the mixture, and stirred for 15 minutes at −78° C. The reaction mixture was acidified by adding 2N hydrochloric acid and extracted with ethyl acetate. The organic layer was washed with water and a saturated aqueous solution of sodium chloride, successively, dried over anhydrous magnesium sulfate and concentrated under reduced pressure. The residue was purified by column on silica gel (hexane:ethyl acetate=5:1) to give the title compound (875 mg) having the following physical data.

TLC: Rf 0.33 (hexane:ethyl acetate=5:1).

Reference example 6

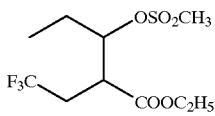

The compound obtained in reference example 5 (875 mg) was dissolved into a mixture solution of dichloromethane (10 ml) and triethylamine (1 ml). The mixture was cooled at 0° C. Methanesulfonyl chloride (0.446 ml) was dropped to the mixture. The mixture was stirred for 30 minutes at 0° C. The reaction mixture was poured into water, and extracted with ether. The organic layer was washed with water and a saturated aqueous solution of sodium chloride, successively, dried over anhydrous magnesium sulfate and concentrated under reduced pressure. The residue was purified by column on silica gel (hexane:ethyl acetate=10:1) to give the title compound (540 mg) having the following physical data.

TLC: Rf 0.33 (hexane:ethyl acetate=2:1).

Reference example 7

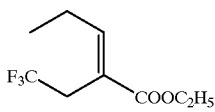

To a solution of the compound obtained in reference example 6 (540 mg) in benzene (6 ml), 1,8-diazabicyclo[5.4.0]undec-7-ene (DBU) (1 ml) was dropped. The mixture was refluxed for 2 hours. The reaction mixture was poured into water, and extracted with ether. The organic layer was washed with 2N hydrochloric acid, water and a saturated aqueous solution of sodium chloride, successively, dried over anhydrous magnesium sulfate and concentrated under reduced pressure. The residue was purified by column on silica gel (hexane:ethyl acetate=30:1) to give the title compound (335 mg) having the following physical data.

TLC: Rf 0.55 (hexane:ethyl acetate=5:1).

Example 1

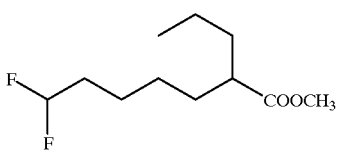

To a solution of the compound obtained in reference example 3 (275 mg) in ethanol (3 ml), 10% palladium on carbon (30 mg) was added, under an atmosphere of argon. The mixture was stirred vigorously for 8 hours at room temperature under an atmosphere of hydrogen. The reaction mixture was filtered through Celite and the filtration was concentrated under reduced pressure to give the title compound having the following physical data.

TLC: Rf 0.62 (hexane:ethyl acetate=10:1).

Example 2

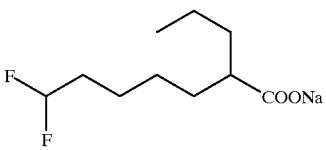

To a solution of the compound obtained in example 1 in ethanol (8 ml), 5N aqueous solution of sodium hydroxide (2 ml) was added. The mixture was stirred for 2 hours at 70° C. The reaction mixture was concentrated under reduced pressure. The residue was acidified by adding 2N hydrochloric acid and extracted with ethyl acetate. The organic layer was washed with water and a saturated aqueous solution of sodium chloride, successively, dried over anhydrous magnesium sulfate and concentrated under reduced pressure. The residue was purified by column on silica gel (hexane:ethyl acetate=5:1–2:1) to give the compound of free acid (238 mg). To the above compound in ethanol (5 ml), 1N aqueous solution of sodium hydroxide (1.06 ml) was added. The mixture was concentrated under reduced pressure to give the title compound having the following physical data.

TLC: Rf 0.21 (hexane:ethyl acetate=5:1);

IR: ν 3392, 2935, 2871, 1557, 1456, 1416, 1318, 1173, 1123, 1058 cm$^{-1}$;

NMR: δ 5.87 (1H,tt), 2.22 (1H,m), 1.98–1.23 (12H, m), 0.94 (3H, t).

Example 2(1)—2(10)

The following compounds were obtained by the same procedure as a series of reaction of reference example 1→reference example 2→reference example 3→example 1→example 2 or reference example 1→reference example 3→example 1→example 2 or reference example 1→example 1→example 2, using a corresponding aldehyde.

Example 2(1)

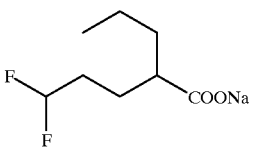

TLC: Rf 0.24 (hexane:ethyl acetate=3:1);

IR (KBr): ν 3436, 2963, 2937, 2875, 1639, 1558, 1495, 1412, 1326, 1195, 1123, 1048, 964, 583 cm$^{-1}$;

NMR: δ 5.89 (1H, tt), 2.23 (1H, m), 1.2–2.0 (8H, m), 0.95 (3H, t).

Example 2(2)

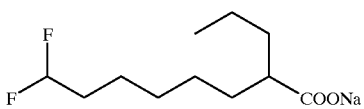

TLC: Rf 0.01 (hexane:ethyl acetate=10:1);

IR: ν 3366, 2934, 2863, 1557, 1416, 1124, 1032 cm$^{-1}$;

NMR: δ 5.87 (1H, tt), 2.23 (1H, m), 1.20–2.00 (14H, m), 0.94 (3H, t).

Example 2(3)

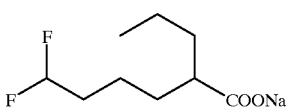

TLC: Rf 0.64 (hexane:ethyl acetate=1:1);

IR (KBr): ν 3401, 2874, 1564, 1447, 1417, 1380, 1320, 1182, 1121, 1048, 1005, 835, 755, 559, 427 cm$^{-1}$;

NMR: δ 5.87 (1H, tt), 2.24 (1H, m), 1.20–2.00 (10H, m), 0.95 (3H, t).

Example 2(4)

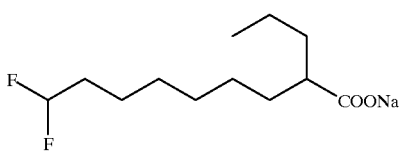

TLC: Rf 0.55 (hexane:ethyl acetate=2:1);

IR: ν 3368, 2932, 2860, 1556, 1445, 1418, 1124, 1039, 859, 727 cm$^{-1}$;

NMR: δ 5.87 (1H, tt), 2.22(1H, m), 1.20–2.00 (1 6H, m), 0.94 (3H, t).

Example 2(5)

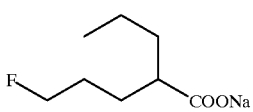

TLC: Rf 0.41 (hexane:ethyl acetate=2:1);

IR (KBr): ν 3651, 3436, 2961, 2936, 2874, 1640, 1553, 1458, 1412, 1322, 1113, 1021, 935, 563 cm$^{-1}$;

NMR: δ 4.40(2H, td), 2.21 (1H, m), 1 .25–1.85 (8H, m), 0.91 (3H, t).

Example 2(6)

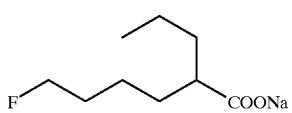

TLC: Rf 0.61 (hexane:ethyl acetate=1:1);

IR (KBr): ν 3402, 2935, 2873, 1561, 1459, 1415, 1321, 1112,1037, 750, 560 cm$^{-1}$;

NMR: δ 4.43 (2H, td), 2.23 (1H, m), 1.20–1.90 (10H, m), 0.95 (3H, t).

Example 2(7)

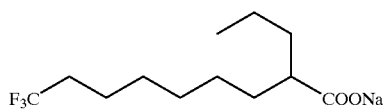

TLC: Rf 0.43 (hexane:ethyl acetate=2:1);

IR: ν 3436, 2936, 2862, 1556, 1467, 1443, 1418, 1390, 1337, 1257, 1211, 1178, 1145, 1041, 837, 728; 656, 567cm$^{-1}$;

NMR: δ 2.33–1.94 (3H, m), 1.67–1.18 (14H, m), 0.90 (3H, t).

Example 2(8)

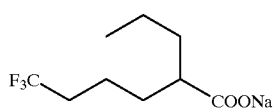

TLC: Rf 0.36 (hexane:ethyl acetate=2:1);

IR (KBr): ν 3401, 2982, 2937, 1561, 1466, 1446, 1418, 1392, 1360, 1311, 1257, 1209, 1153, 1097, 1041, 1017, 926, 846, 756, 656, 551, 422 cm$^{-1}$;

NMR: δ 2.30–1.90 (3H, m), 1.75–1.15 (8H, m), 0.91 (3H, t).

Example 2(9)

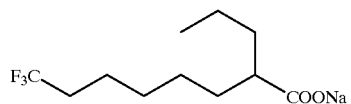

TLC: Rf 0.49 (hexane:ethyl acetate=2:1);

IR (KBr): ν 3431, 2937, 2863, 1639, 1554, 1460, 1443, 1415, 1390, 1319, 1257, 1190, 1146, 1037, 838, 656 cm$^{-1}$;

NMR: δ 2.35–1.95 (3H, m), 1.70–1.10 (12H, m), 0.90 (3H, t).

Example 2(10)

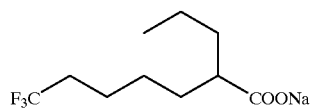

TLC: Rf 0.36 (hexane:ethyl acetate=3:1);

IR (KBr): ν 3436, 2937, 2876, 1736, 1555, 1459, 1420, 1390, 1336, 1256, 1200, 1148, 1083, 1026, 839, 656 cm$^{-1}$;

NMR: δ 2.30–1.95 (3H, m), 1.74–146 (10H, m), 0.90 (3H, t).

Example 2(11)–2(12)

The following compounds were obtained by the same procedure as a series of example 1→example 2, using the compound obtained in reference example 7 or the compound obtained by the same procedure as a series of reference example 5→reference example 6→reference example 7, using a corresponding compound.

Example 2(11)

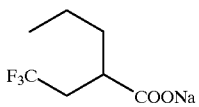

TLC: Rf 0.40 (hexane:ethyl acetate=2:1);

IR (KBr): ν 3436, 2965, 2879, 1572, 1439, 1416, 1377, 1328, 1254, 1158, 1117, 1083, 995, 957, 866, 830, 743, 660, 625, 592, 515 cm$^{-1}$;

NMR: δ 2.73–2.40 (2H, m), 2.25–1.94 (1H, m), 1.70–1.25 (4H, m), 0.92 (3H, t).

Example 2(12)

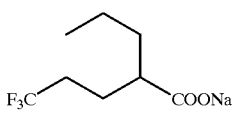

TLC: Rt 0.22 (hexane:ethyl acetate=3:1);

IR (KBr): ν 3431, 2960, 2876, 1562, 1460, 1418, 1389, 1340, 1306, 1257, 1227, 1155, 1099, 1051, 985, 907, 858, 572 cm$^{-1}$;

NMR: δ 2.30–1.90 (3H, m), 1.80–1.20 (6H, m), 0.92 (3H, t).

Example 3

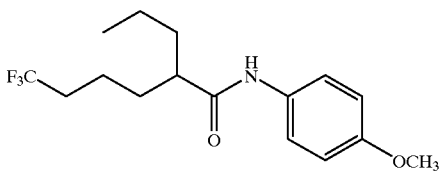

To a solution of the compound of free acid obtained in example 2(8) (0.5 g), oxalyl chloride (1.85 ml) was added at room temperature. The mixture was stirred for 2 hours at room temperature. The reaction mixture was concentrated under reduced pressure to give acyl chloride. A solution of acyl chloride in ether (2 ml) was dropped to a solution of 4-methoxyaniline (218 mg) and triethylamine (1 ml) in diethylether (10 ml) at 0° C. The mixture was stirred for 1 hour. The reaction mixture was washed with 2N hydrochloride, water and a saturated aqueous solution of sodium chloride, successively, dried over anhydrous magnesium sulfate and concentrated under reduced pressure. The residue was recrystallized from a mixture of n-hexane and ethyl acetate (10:1) to give the title compound (412 mg) having the following physical data.

TLC: Rf 0.43 (hexane:ethyl acetate=2:1);

IR (KBr): ν 3449, 3243, 2951, 2870, 1655, 1603, 1546, 1515, 1459, 1445, 1417, 1393, 1364, 1321, 1286, 1252, 1212, 1199, 1182, 1144, 1131, 1093, 1036, 832, 741, 656, 558, 529, 430 cm$^{-1}$;

NMR (CDCl$_3$+CD$_3$OD): δ 7.46 (2H, d), 6.86 (2H, d), 3.80 (3H, s), 2.38–1.95 (3H, m), 1.85 (8H, m), 0.92 (3H, t).

Example 3(1)–3(5)

The following compounds were obtained by the same procedure as a series of reaction of example 3 or example 3→example 1, using corresponding compounds instead of 4-methoxyaniline in example 3.

Example 3(1)

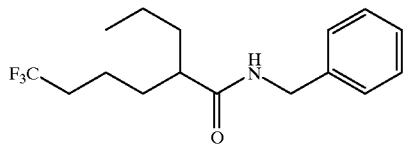

TLC: Rf 0.63 (hexane:ethyl acetate=2:1);

IR (KBr): ν 3280, 3090, 2955, 2875, 1640, 1553, 1498, 1459, 1393, 1357, 1286, 1255, 1220, 1206, 1155, 1136, 1098, 1045, 1027, 1004, 836, 743, 693, 658, 580, 539, 491, 426 cm$^{-1}$;

NMR: δ 7.45–7.10 (5H, m), 5.90–5.60 (1H, br), 4.45 (2H, d), 2.20–1.85 3H, m), 1.80–1.10 (8H, m), 0.90 (3H, t).

Example 3(2)

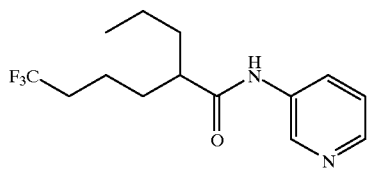

TLC: Rf 0.38 (chloroform:methanol=10:1);

IR (KBr): ν 3293, 3253, 3189, 3133, 2955, 2875, 1660, 1603, 1547, 1484, 1467, 1413, 1396, 1329, 1298, 1261, 1201, 1147, 1098, 1053, 1021, 942, 887, 813, 747, 712, 636 cm$^{-1}$;

NMR: δ 8.56 (1H, d), 8.35 (1H, d), 8.21 (1H, dd), 7.61 (1H, s), 7.30 (1H, dd), 2.35–1.90 (3H, m), 1.90–1.20 (8H, m), 0.93 (3H, t).

Example 3(3)

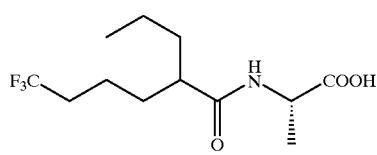

TLC: Rf 0.20 (chloroform:methanol=10:1);

[α]$_D$–25.39 (c=1.01, EtOH)

IR (KBr): ν 3293, 3089, 2940, 2878, 1719, 1646, 1547, 1466, 1397, 1377, 1360, 1327, 1287, 1260, 1222, 1210, 1132, 1054, 1025, 946, 837, 659, 592, 422 cm$^{-1}$;

NMR: δ 9.20–8.60 (1H, br), 6.40–6.00 (1H, br), 4.75–4.40 (1H, br), 2.30–1.10 (11H, br), 1.00–0.85 (3H, br).

Example 3(4)

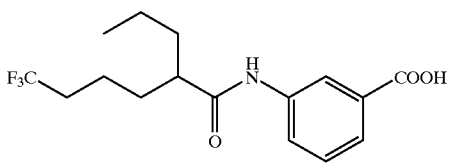

TLC: Rf 0.29 (chloroform:methanol=10:1);

IR (KBr): ν 3302, 2960, 2876, 2664, 1694, 1661, 1591, 1552, 1451, 1414, 1359, 1288, 1257, 1194, 1148, 1093, 1050, 1016, 948, 911, 815, 756, 685, 665, 665, 564cm$^{-1}$;

NMR (CDCl$_3$+CD3OD): δ 8.07 (1H, dd), 7.98 (1H, d), 7.78 (1H, dd), 7.41 (1H, t), 2.42–1.90 (3H, m), 1.85–1.15 (8H, m), 0.93 (3H, t).

Example 3(5)

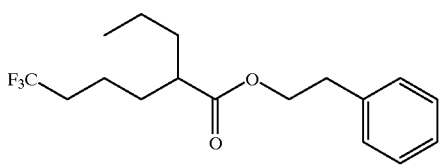

TLC: Rf 0.54 (hexane:ethyl acetate=5:1);

IR (KBr): ν 3031, 2960, 2875, 1733, 1498, 1456, 1392, 1256, 1210, 1148, 748, 700cm$^{-1}$;

NMR (CDCl$_3$): δ 7.30–7.19 (5H, m), 4.32 (2H, t), 2.94 (2H, t), 2.40–2.25 (1H, m), 2.10–1.85 (2H, m), 1.80–1.10 (8H, m), 0.86 (3H, t).

Reference example 4

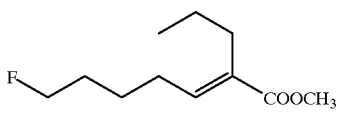

A solution of the compound obtained in reference example 1 (400 mg) in anhydrous dichloromethane (2 ml) was dropped to a solution of DAST (316 μl) in anhydrous dichloromethane (2 ml) under an atmosphere of argon at -78° C. The mixture was stirred for 1.5 hours at 0° C. The reaction mixture was diluted with ether, washed with water and a saturated aqueous solution of sodium chloride, successively, concentrated under reduced pressure. The residue was purified by column on silica gel (hexane:ethyl acetate=20:1) to give the title compound (132 mg) having the following physical data.

TLC: Rf 0.67 (hexane:ethyl acetate=3:1).

Example 4

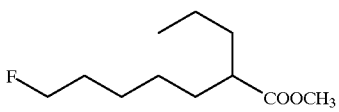

To a solution of the compound obtained in reference example 4 (132 mg) in ethanol (2 ml), 10% palladium on carbon (10 mg) was added, under an atmosphere of argon. The mixture was stirred vigorously for 2 hours at room temperature under an atmosphere of hydrogen. The mixture was filtered through Celite and washed with ethyl acetate. The organic layer was concentrated under reduced pressure to give the title compound having the following physical data.

TLC: Rf 0.48 (hexane:ethyl acetate=10:1).

Example 5

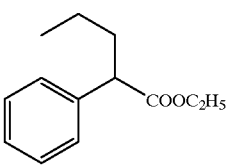

To a solution of diisopropylamine (1.3 ml) in anhydrous tetrahydrofuran (10 ml), a solution of 1.6M n-butyllithium in hexane (4.6 ml) was dropped, under an atmosphere of argon at 0° C. The mixture was stirred for 30 minutes. To the reaction solution, a solution of ethyl phenyl acetate (1.00 g) in tetrahydrofuran (3 ml) was dropped, at -78° C. The mixture was stirred for 40 minutes. To the reaction solution, a mixture of a solution of 1-iodopropane (1.24 g) in tetrahydrofuran (2 ml) and hexamethyl phospholamide (2 ml) was dropped. The mixture was stirred for 3 hours. The reaction mixture was diluted with ether, washed with a saturated aqueous solution of ammonium chloride, water and a saturated aqueous solution of sodium chloride, successively, dried over anhydrous magnesium sulfate and concentrated under reduced pressure. The residue was purified by column on silica gel (hexane:ethyl acetate=40:1) to give the title compound (788 mg) having the following physical data.

TLC: Rf 0.43 (hexane:ethyl acetate=20:1).

Example 6

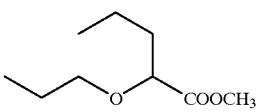

To a solution of methyl 2-hydoxypentanoate (300 mg) in dimethylformamide (3 ml), sodium hydride (109 mg) was added, under an atmosphere of argon at 0° C. The mixture was stirred for 30 minutes at room temperature. 1-Iodopropane (266 μl) was dropped to the reaction mixture. The mixture was stirred for 8 hours. The reaction mixture was diluted with ether, washed with water and a saturated aqueous solution of sodium chloride, successively, dried over anhydrous magnesium sulfate and concentrated under reduced pressure. The residue was purified by column on silica gel (hexane:ethyl acetate=30:1) to give the title compound (91 mg) having the following physical data.

TLC: Rf 0.75 (hexane:ethyl acetate=3:1).

Example 7

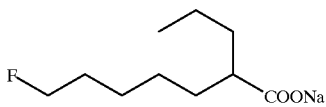

To a solution of the compound obtained in example 4 in ethanol (2 ml), 5N aqueous solution of sodium hydroxide (0.5 ml) was added. The mixture was stirred for 2 hours at 60° C. The reaction mixture was concentrated under reduced pressure. The residue was acidified by adding 2N hydrochloric acid and extracted with ethyl acetate. The organic layer was washed with water and a saturated aqueous solution of sodium chloride, successively, dried over anhydrous magnesium sulfate and concentrated under reduced pressure. The residue was purified by column on silica gel (hexane:ethyl acetate=4:1–2:1) to give the compound of free acid (112 mg). To the above compound in ethanol (2 ml), 1N aqueous solution of sodium hydroxide (534 μl) was added. The mixture was concentrated under reduced pressure to give the title compound having the following physical data.

TLC: Rf 0.12 (hexane:ethyl acetate=4:1);

IR: ν 3368, 2934, 2862, 1557, 1455, 1417, 1318, 1044, 749 cm$^{-1}$;

NMR: δ 4.43 (2H,td), 2.23 (1H,m), 1.85–1.20 (12H, m), 0.94 (3H, t).

Example 7(1)—7(22)

The following compounds were obtained by the same procedure as a series of reaction of reference example 1→reference example 4→example 4→example 7 or reference example 1→example 4→example 7, using a corresponding aldehyde.

Example 7(1)

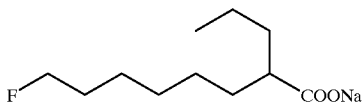

TLC: Rf 0.38 (hexane:ethyl acetate=3:1);

NMR: δ 4.43 (2H, td), 2.23 (1H,m), 1.22–1.89 (14H, m), 0.95 (3H, t).

Example 7(2)

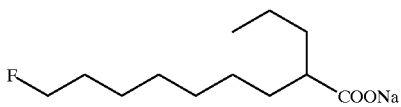

TLC: Rf 0.74n (hexane:ethyl acetate=2:1);

NMR: δ4.43 (2H, td), 2.22 (1H, m), 1.20–1.85 (1 6H, m), 0.94 (3H, t).

Example 7(3)

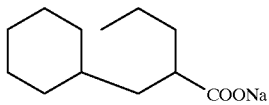

TLC: Rf 0.33 (hexane:ethyl acetate=4:1);

NMR: δ 2.32 (1H, m), 1.97–1.80 (1H, br), 1.77–1.03 (14H, m), 1.00–0.70 (5H, m).

Example 7(4)

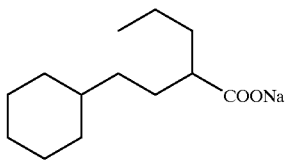

TLC: Rf 0.29 (hexane:ethyl acetate=4:1);

NMR: δ 2.13 (1H, m), 1.80–1.05 (17H, m), 1.00–0.73 (5H, m).

Example 7(5)

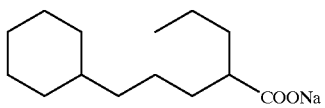

TLC: Rf 0.35 (hexane:ethyl acetate=4:1);

NMR: δ 2.17 (1H, m), 1.78–1.05 (19H, m), 1.00–0.70 (5H, m).

Example 7(6)

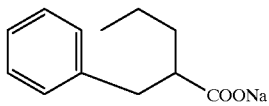

TLC: Rf 0.32 (hexane:ethyl acetate=3:1);

NMR: δ 7.30–7.05 (5H, m), 3.00–2.85 (1H, m), 2.70–2.40 (2H, m), 1.70–1.10 (4H, m), 0.87 (3H, t).

Example 7(7)

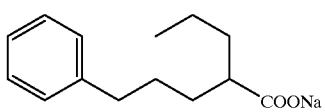

TLC: Rf 0.30 (hexane:ethyl acetate=4:1);

NMR δ 7.30–7.00 (5H, m), 2.60 (2H, t), 2.21 (1H, m), 1.75–1.15 (8H, m), 0.89 (3H, t).

Example 7(8)

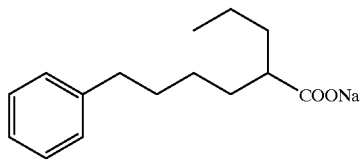

TLC: Rf 0.31 (hexane:ethyl acetate=3:1);

NMR: δ 7.35–7.00 (5H, m), 2.58 (2H, t), 2.30–2.05 (1H, m), 1.80–1.10 (10H, m), 0.89 (3H, t).

Example 7(9)

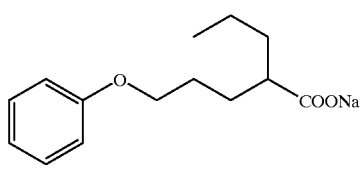

TLC: Rf 0.21 (hexane:ethyl acetate=5:1);

NMR: δ 7.20 (2H, m), 6.92 (3H, m), 3.99 (2H, m), 2.27 (1H, m), 1.31–1.89 (8H, m), 0.95 (3H, m).

Example 7(10)

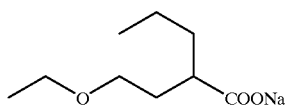

TLC: Rf 0.26 (hexane:ethyl acetate=3:1);

NMR: δ 83.55–3.35 (4H, m), 2.36–2.15 (1H, m), 1.95–1.23 (6H, m), 1.16 (3H, t), 0.91 (3H, t).

Example 7(11)

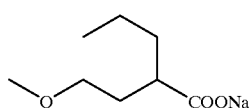

TLC: Rf 0.16 (hexane:ethyl acetate=2:1);

NMR: δ 3.40 (2H, t), 3.29 (3H, s), 2.35–2.15 (1H, br), 1.92–1.20 (6H, m), 0.91 (3H, t).

Example 7(12)

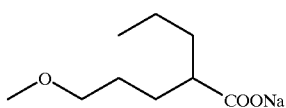

TLC: Rf 0.32 (hexane:ethyl acetate=1:1);

NMR: δ 3.50–3.20 (5H, m), 2.30–2.05 (1H, br), 1.75–1.15 (8H, m), 0.90 (3H, t).

Example 7(13)

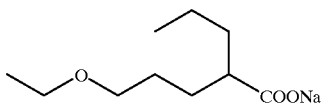

TLC: Rf 0.41 (hexane:ethyl acetate=1:1);

NMR: δ 3.55–3.38 (4H, m), 2.30–2.08 (1H, m), 1.70–1.20 (8H, m), 1.16 (3H, t), 0.90 (3H, t).

Example 7(14)

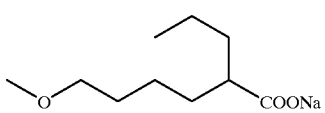

TLC: Rf 0.32 (hexane:ethyl acetate=1:1);

NMR δ 3.45–3.30 (2H, m), 3.30 (3H, s), 2.30–2.05 (1H, m), 1.70–1.15 (10H, m), 0.95–0.80 (3H, br).

Example 7(15)

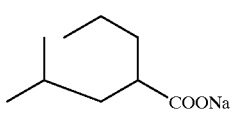

TLC: Rf 0.22 (hexane:ethyl acetate 10:1);

NMR: δ 2.32 (1H, m), 1.02–1.74 (7H, m), 0.92 (9H, m).

Example 7(16)

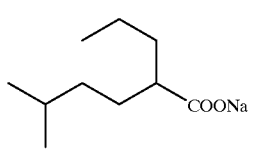

TLC: Rf 0.38 (hexane:ethyl acetate=4:1);

NMR: δ 2.15 (1H, m), 1.70–1.10 (9H, m), 1.00–0.75 (9H, m).

Example 7(17)

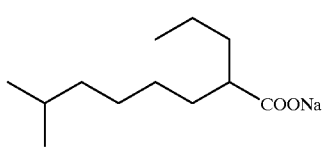

TLC: Rf 0.34 (hexane:ethyl acetate=3:1);

NMR: δ 2.25–2.08 (1H, m), 1.65–1.05 (13H, m), 0.90 (3H, t), 0.87 (6H, d).

Example 7(18)

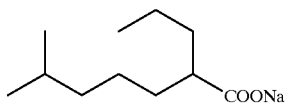

TLC: Rf 0.35 (hexane:ethyl acetate=3:1);

NMR: δ 2.30–2.05 (1H, m), 1.67–1.07 (11H, m), 0.90 (3H, t), 0.87 (6H, d).

Example 7(19)

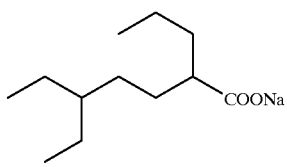

TLC: Rf 0.34 (hexane:ethyl acetate=3:1);

NMR: δ 2.22–2.05 (1H, m), 1.65–1.05 (13H, m), 0.88 (3H, t), 0.85 (6H, t).

Example 7(20)

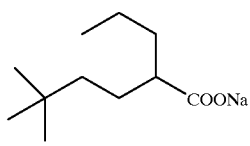

TLC: Rf 0.29 (hexane:ethyl acetate=5:1);

NMR: δ 2.20–2.00 (1H, br), 1.65–1.10 (8H, m), 0.95–0.80 (12H, m).

Example 7(21)

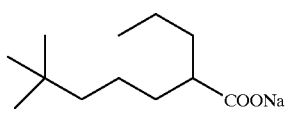

TLC: Rf 0.53 (hexane:ethyl acetate 3:1);

NMR: δ 2.24 (1H, m), 1.13–1.70 (10H, m), 0.92 (12H, m).

Example 7(22)

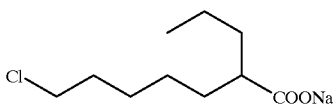

TLC: Rf 0.47 (chloroform:methanol 10:1);

NMR: δ 3.53 (2H, t), 2.28–2.10 (1H, m), 2.85–1.20 (12H, m), 0.90 (3H, t).

Example 7(23)–7(33)

The following compounds were obtained by the same procedure as in example 7 using the compound obtained in example 5 or the compound obtained by same procedure as in example 5 using a corresponding acetate instead of ethyl phenyl acetate in example 5 or the compound obtained by the same procedure as in example 5 using corresponding pentanoate instead of ethyl phenyl acetate and corresponding compound instead of 1-iodopropane in example 5, or by the same procedure as a series of reaction of example 5→example 4→example 7, using a corresponding carboxylate instead of ethyl phenyl acetate and 3-bromo-1 -propen instead of 1-iodopropane.

Example 7(23)

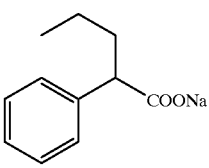

TLC: Rf 0.27 (hexane:ethyl acetate=1:1);

NMR: δ 7.40 (2H, m), 7.20 (3H, m), 3.45 (1H, m), 2.00 (1H, m), 1.65 (1H, m), 1.30 (2H, m), 0.95 (3H, t).

Example 7(24)

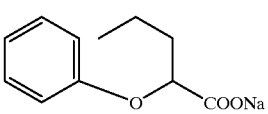

TLC: Rf 0.12 (hexane:ethyl acetate=1:1);

NMR: δ 7.20 (2H, m), 6.90 (3H, m), 4.35 (1H,m), 1.90 (2H, m), 1.55 (2H, m), 0.95 (3H, m).

Example 7(25)

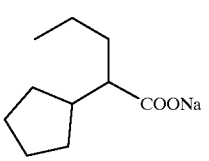

TLC: Rf 0.24 (hexane:ethyl acetate=10:1);

NMR: δ 1.02–2.05 (14H, m), 0.92 (3H, t).

Example 7(26)

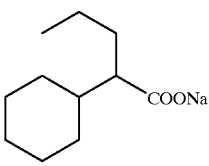

TLC: Rf 0.5 (hexane:ethyl acetate=3:1);

NMR: δ 1.00–2.04 (16H, m), 0.94 (3H, t).

Example 7(27)

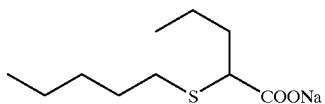

TLC: Rf 0.56 (hexane:ethyl acetate=1:1);

NMR: δ 3.24 (1H, dd), 2.63 (1H, t), 2.60 (1H, t), 1.30–1.90 (10H, m), 0,97 (3H, t), 0.94 (3H, t).

Example 7(28)

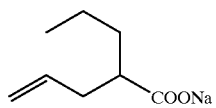

TLC: Rf 0.11 (hexane:ethyl acetate=10:1);

NMR: δ 5.85 (1H, m), 4.98 (2H, m), 2.00–2.50 (3H, m), 1.20–1.70 (4H, m), 0.93 (3H, m).

Example 7(29)

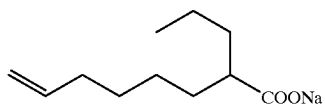

TLC: Rf 0.29 (hexane:ethyl acetate=3:1);

NMR: δ 5.80 (1H, m), 5.03–4.90 (2H, m), 2.27–1.95 (3H, m), 1.65–1.15 (10H, m), 0.89 (3H, t).

Example 7(30)

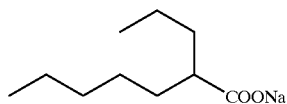

TLC: Rf 0.31 (hexane:ethyl acetate 5:1);

NMR: δ 2.19 (1H, m), 1.65–1.12 (12H, m), 0.90 (3H, t), 0.89 (3H, t).

Example 7(31)

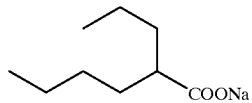

TLC: Rf 0.37 (hexane:ethyl acetate=5:1);

NMR: δ 2.30–2.07 (1H, m), 1.65–1.10 (10H, m), 0.95–0.75 (6H, m).

Example 7(32)

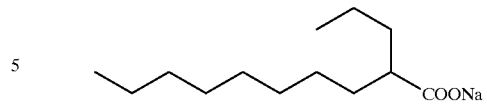

TLC: Rf 0.31 (hexane:ethyl acetate=5:1);

NMR: δ 2.27–2.08 (1H, m), 1.65–1.15 (18H, m), 0.95–0.85 (6H, m).

Example 7(33)

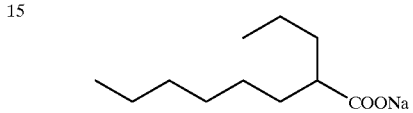

TLC: Rf 0.50 (hexane:ethyl acetate=3:1);

NMR δ 2.25 (1H, m), 1.20–1.70 (14H, m), 0.93 (6H, m).

Example 7(34)–7(38)

The following compounds were obtained by the same procedure as in example 7 using the compound obtained in example 6 or the compound obtained by the same procedure as in example 6 using a corresponding iodoalkane instead of 1-iodopropane in example 6.

Example 7(34)

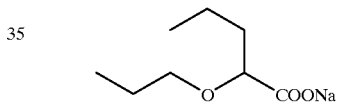

TLC: Rf 0.11 (hexane ethyl acetate=1:1);

NMR: δ 3.45–3.65 (2H, m), 3.71 (1H, td), 1.30–1.70 (6H, m), 0.91 (6H, t).

Example 7(35)

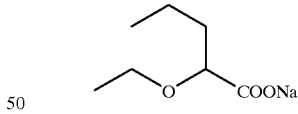

TLC: Rf 0.29 (hexane:ethylacetate=10:1);

NMR: δ 3.64 (2H, m), 3.35 (1H, q), 1.72–1.25 (4H, m), 1.19 (3H, t), 0.92 (3H, t).

Example 7(36)

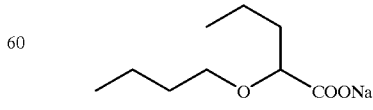

TLC: Rf 0.5 (ethyl acetate);

NMR: δ 3.66 (2H, m), 3.28 (1H, m), 1.32–1.74 (8H, m), 0.96 (6H, t).

Example 7(37)

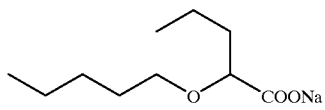

TLC: Rf 0.5 (ethyl acetate);

NMR: δ 3.66 (2H, m), 3.26 (1H, m), 1.30–1.76 (10H, m), 0.96 (6H, t).

Example 7(38)

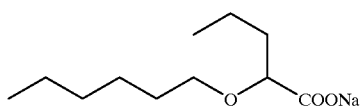

TLC: Rf 0.12 (hexane:ethyl acetate=1:1);

NMR: δ 3.67 (2H, m), 3.30–3.15 (1H, m), 1.72–1.10 (12H, m), 0.98–0.83 (6H, m).

Example 8

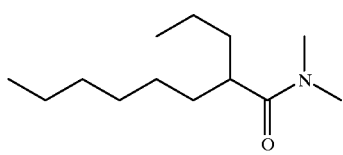

To a solution of 2-propyloctanoic acid (500 mg) in anhydrous benzene (5 ml), oxalyl chloride (350 ml) was added at room temperature. The mixture was stirred for 30 minutes at 50° C. The reaction mixture was concentrated under reduced pressure to give acyl chloride. A solution of the acyl chloride in tetrahydrofuran (3 ml) was dropped to a solution of 50% dimethylamine (3 ml) at 0° C. The mixture was stirred 1 hour. The reaction mixture was diluted with ether, washed with 2N hydrochloride, water and a saturated aqueous solution of sodium chloride, successively, dried over anhydrous magnesium sulfate and concentrated under reduced pressure. The residue was purified by column on silica gel (hexane:ethyl acetate=2:1) to give the title compound (412 mg) having the following physical data.

TLC: Rf 0.43 (hexane:ethyl acetate=2:1);

IR: ν 2957, 2928, 2857, 1661, 1646, 1466, 1414, 1397, 1337, 1262, 1155, 1111 cm$^{-1}$;

NMR (CDCl$_3$): δ 3.04 (3H, s), 2.96 (3H, s), 2.65 (1H, m), 1.10–1.85 (14H, m), 0.87 (3H, t), 0.86 (3H, t).

Example 8(1)–8(6)

The following compounds were obtained by the same procedure as in example 8 using a corresponding carboxylic acid and a corresponding amine.

Example 8(1)

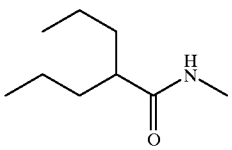

TLC: Rf 0.19 (hexane:ethyl acetate=2:1);

NMR: δ 5.70–5.30 (1H, br), 2.81 (3H, d), 2.02 (1H, m), 1.80–1.10 (8H, m), 0.89 (6H, t).

Example 8(2)

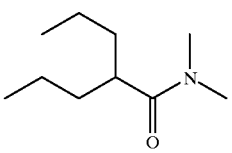

TLC: Rf 0.30 (hexane:ethyl acetate=2:1);

NMR: δ 3.06 (3H, s), 2.97 (3H, s), 2.68 (1H, m), 1.75–1.45 (2H, m), 1.45–1.10 (6H, m), 0.89 (6H, t).

Example 8(3)

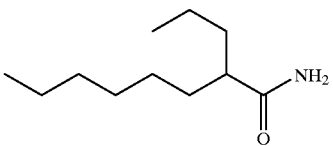

TLC: Rf 0.22 (hexane:ethyl acetate=2:1);

NMR (CDCl$_3$): δ 5.64 (1H, brs), 5.43 (1H, brs), 2.11 (1H, m), 1.10–1.80 (14H, m), 0.90 (3H, t), 0.86 (3H, t).

Example 8(4)

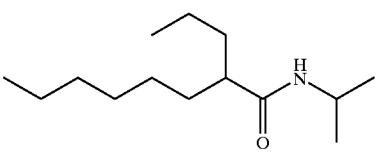

TLC: Rf 0.64 (hexane:ethyl acetate 2:1);

NMR (CDCl$_3$): δ 5.22 (1H, brd), 4.10 (1H, m), 1.91 (1H, m), 1.18–1.75 (14H, m), 1.14 (6H, d), 0.88 (3H, t), 0.86 (3H, t).

Example 8(5)

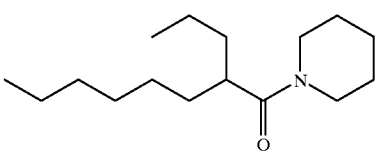

TLC: Rf 0.41 (hexane:ethyl acetate=4:1);

NMR: δ 3.59 (2H, t), 3.49 (2H, t), 2.73–2.58 (1H, m), 1.75–1.45 (9H, m), 1.45–1.10 (11H, m), 0.93–0.81 (6H, m).

Example 8(6)

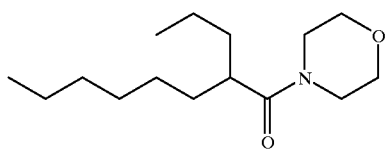

TLC: Rf 0.20 (hexane:ethyl acetate=4:1);

NMR: δ 3.67 (4H, s), 3.68–3.60 (2H, m), 3.59–3.49 (2H, m), 2.69–2.52 (1H, m), 1.74–1.51 (2H, m), 1.50–1.08 (12H, m), 0.93–0.80 (6H, m).

Example 9

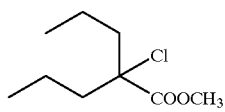

To a solution of diisopropylamine (1.6 ml) in anhydrous THF (10 ml), 1.6 M n-butyllithium in hexane (5.9 ml) was dropped under an atmosphere of argon at 0° C. The mixture was stirred for 30 minutes. A solution of methyl 2-propylpentanoate (1.00 g) in THF (3 ml) was dropped to the reaction mixture at −78° C. The mixture was stirred for 15 minutes and then 20 minutes. A solution of carbon tetrachloride (1.17 g) in THF (2 ml) was added to the reaction mixture at −78° C. The mixture was stirred for 80 minutes at room temperature. 1N Hydrochloride was added to the reaction mixture. The mixture was diluted with ether, washed with water and a saturated aqueous solution of sodium chloride, successively, dried over anhydrous magnesium sulfate and concentrated under reduced pressure. The residue was purified by column on silica gel (hexane:ethyl acetate=40:1) to give the title compound (1.37 mg) having the following physical data.

TLC: Rf 0.45 (hexane:ethyl acetate=10:1);

NMR (CDCl$_3$): δ 3.76 (3H, s), 2.1–1.8 (4H, m), 1.6–1.1 (4H, m), 0.92 (6H, t).

Example 10

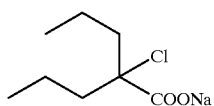

To a solution of the compound obtained in example 9 (600 mg) in anhydrous ether (10 ml), lithium aluminum hydride (119 mg) was added, under an atmosphere of argon at 0° C. The mixture was stirred for 30 minutes. The reaction mixture was diluted with ether, washed with a saturated aqueous solution of sodium chloride, dried over anhydrous magnesium sulfate and concentrated under reduced pressure. The residue was purified by column on silica gel (hexane:ethyl acetate=10:1) to give the 2-chloro-2-propylpentanol. To a solution of the above compound in anhydrous dichloromethane (14 ml), 4A molecular sieves (1.5 g) and pyridinium dichromate (1.29 g) was added, under an atmosphere of argon. The mixture was stirred for 3 hours at room temperature. The reaction mixture was diluted with ether, filtrated by silica gel. The filtration was concentrated under reduced pressure. The residue was purified by column on silica gel (hexane:ethyl acetate=40: 1). To a solution of the obtained aldehyde compound in t-butanol (3 ml), 2-methyl-2-butene (0.2 ml) was added. And then an aqueous solution of sodium chlorite (248 mg) and sodium phosphate monobasic dihydrate (215 mg) in water (1 ml) was added to the mixture. The mixture was stirred for 30 minutes at room temperature. The reaction mixture was diluted with ethyl acetate, washed water and a saturated aqueous solution of sodium chloride, successively, dried over anhydrous magnesium sulfate and concentrated under reduced pressure. The residue was purified by column on silica gel (hexane:ethyl acetate=1:1) to give the compound of free acid (150 mg). To the above compound in ethanol (3 ml), 1N aqueous solution of sodium hydroxide (800 ml) was added. The mixture was concentrated under reduced pressure to give the title compound (134 mg) having the following physical data.

TLC: Rf 0.11 (hexane ethyl acetate=10:1);

IR (KBr): ν 3449, 2963, 2876, 1600, 1433, 1402, 1132, 763, 665cm$^{-1}$;

NMR: δ 1.28–2.14 (8H, m), 0.95 (6H, t).

Example 11

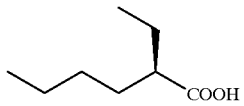

(±)2-Ethylhexanoic acid (5 g) being on the market and quinine (5.6 g) were dissolved under heating into 50% water contained acetone. The mixture was allowed to stand over night. The precipitated crystals was filtered. The crude crystals was dried under pressure, and recrystallized from aqueous acetone (6 times). The crystals were dissolved into diluted hydrochloric acid, extracted with ether. The organic layer was washed water and a saturated aqueous solution of sodium chloride, successively, dried and concentrated under reduced pressure to give the title compound (190 mg) having the following physical data.

[α]$_D$ −8.70 (c=2.59, CHCl$_3$);

IR: ν 2964, 2876, 1708, 1461, 1290, 1231 cm$^{-1}$;

Reference example 8

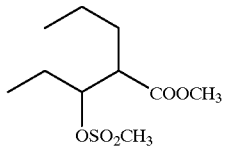

A solution of lithium diisopropylamide in heptane-tetrahydrofuran-ethyl benzene (2M, 5 ml) was added to tetrahydrofuran (THF) (5 ml) under an atmosphere of argon. The mixture was cooled at −70° C. A solution of methyl pentanoate (1.33 ml) in THF (3 ml) was added to the above solution. The mixture was stirred for 30 minutes at −70° C. A solution of propanal (0.72 ml) in THF (3 ml) was dropped to the reaction mixture. The mixture was stirred for 15 minutes at −70° C. To the reaction mixture, a saturated aqueous solution of ammonium chloride was added. The mixture was extracted with ethyl acetate. The organic layer was washed water and a saturated aqueous solution of sodium chloride, successively, dried and concentrated under reduced pressure. The residue was purified by column on silica gel (hexane:ethyl acetate=9:1) to give the hydroxy compound (752 mg). To a solution of the above compound (550 mg) in methylene chloride (10 ml), triethylamine (0.57 ml) was added, under an atmosphere of argon. The mixture was cooled at −20° C. A solution of mesyl chloride (0.29 ml) was dropped to the above solution. The mixture was stirred for 30 minutes at −20° C.−−10° C. The reaction mixture was poured into water with ice, and extracted with ethyl acetate. The extract was washed with a saturated aqueous solution of sodium chloride, dried and concentrated under reduced pressure to give the title compound. The title compound was used the next reaction without a purification process.

Example 12

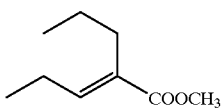

To a solution of the compound obtained in reference example 8 in benzene (10 ml), DBU (0.56 ml) was added, and stirred for 16 hours at room temperature. The reaction solution was poured into cooled 1N hydrochloric acid, and extracted with ethyl acetate. The extract was washed water and a saturated aqueous solution of sodium chloride, successively, dried and concentrated under reduced pressure. The residue was purified by column on silica gel (hexane:ethyl acetate=20:1) to give the title compound (164 mg) and EZ mixture (114 mg).

Example 13

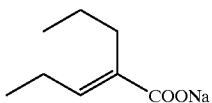

To the E compound obtained in example 12 (160 mg), 1N aqueous solution of sodium hydroxide was added. The mixture was stirred for 1 hour at room temperature, and for 1 hour at 50° C., and then for 12 hours at room temperature. The reaction solution was diluted with ether. Water was added to the above solution. The solution was separated. The water layer was acidified by 1 N hydrochloric acid, extracted with ethyl acetate. The extract was washed water and a saturated aqueous solution of sodium chloride, successively, dried and concentrated under reduced pressure. The residue was purified by column on silica gel (hexane:ethyl acetate= 10:1–2:1) to give the compound of free acid (117 mg). To the above compound in dioxane, 1N aqueous solution of sodium hydroxide was added. The mixture was freeze-dried to give the title compound having the following physical data.

TLC: Rf 0.22 (hexane:ethyl acetate=3:1);

IR (KBr): ν 3436, 2962, 2933, 2872, 1649, 1558, 1461, 1411, 1111 849, 798 cm$^{-1}$.

Formulation example 1
Preparation of tablets
The following compounds were admixed in conventional method and punched out to obtain 100 tablets each containing 100 mg of active ingredient.

| | |
|---|---|
| sodium 5,5,5-trifluoro-2-propylpentanoate | 10 g |
| Cellulose calcium glycolate (disintegrating agent) | 200 mg |
| Magnesium stearate (lubricating agent) | 100 mg |
| Micro crystalline cellulose | 9.7 g |

Formulation example 2
Preparation of tablets
The following compounds were admixed in conventional method and punched out to obtain 100 tablets each containing 100 mg of active ingredient.

| | |
|---|---|
| sodium 2-propylpentanoate | 10 g |
| Cellulose calcium glycolate (disintegrating agent) | 200 mg |
| Magnesium stearate (lubricating agent) | 100 mg |
| Micro crystalline cellulose | 9.7 g |

Figure 1:
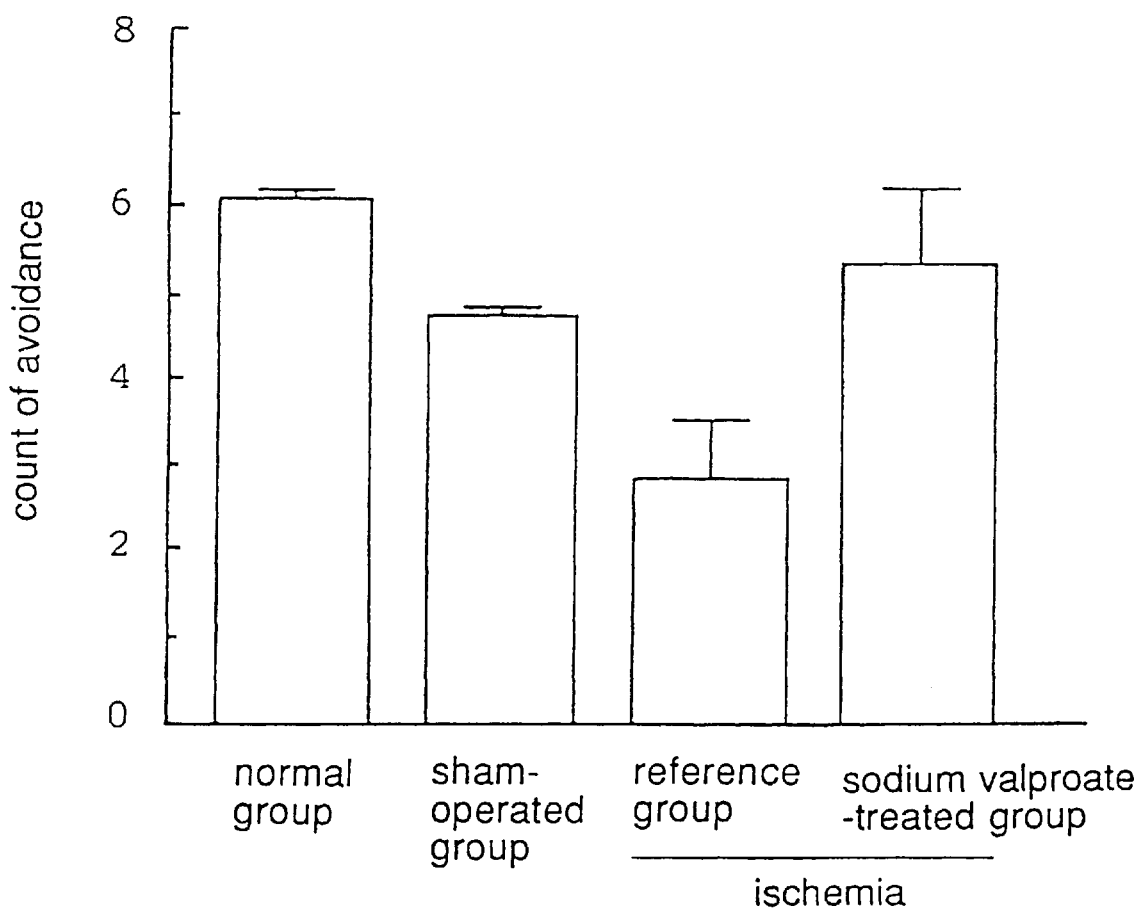
FIG. 1 was indicated an effect on brain ischemia of sodium valproate.

What is claimed is:

1. A method for treating diseases induced by reactive astrocytes, which comprises administering an effective amount of a compound of the formula (X):

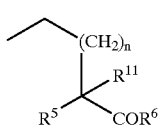

(X)

wherein n is 0 or 1;

$R^{11}$ is hydrogen or chlorine;

$R^5$ is $R^7$—$CH_2$— or $R^8$, or $R^5$ and $R^{11}$, taken together, form C3-10 alkylidene;

$R^7$ is F—$(CH_2)_m$—, in which m is 4–6, $F_3C$—$CH_2$—, C2-10 alkyl substituted by 1 or 2 chlorines, or C1-5 alkyl substituted by 1 or 2 C1-4 alkoxy, C3-7 cycloalkyl, phenyl or phenoxy groups;

$R^8$ is (i) C3-10 alkyl, (ii) C3-10 alkenyl, (iii) C2-10 alkoxy, (iv) C2-10 alkylthio, (v) C3-7 cycloalkyl, (vi) phenyl or (vii) phenoxy;

$R^6$ is hydroxy, or non-toxic salts thereof or acid addition salts thereof.

2. A method according to claim 1, wherein $R^7$ is F—$(CH_2)_m$—, in which m is 4–6, or $F_3C$—$CH_2$—.

3. A method according to claim 1, wherein $R^8$ is C3-10 alkyl.

4. A method according to claim 1, wherein $R^7$ is C2-10 alkyl substituted by 1 or 2 of chlorines, or C1-5 alkyl substituted by 1 or 2 C1-4 alkoxy, C3-7 cycloalkyl, phenyl or phenoxy groups or $R^8$ is C3-10 alkenyl, C2-10 alkoxy, C2-10 alkylthio, C3-7 cycloalkyl, phenyl or phenoxy groups, or $R^5$ and $R^{11}$, taken together are C3-10 alkylidene.

5. A method according to claim 1, wherein the compound
7-fluoro-2-propylheptanoic acid,
8-fluoro-2-propyloctanoic acid,
9-fluoro-2-propylnonanoic acid, or
5,5,5-trifluoro-2-propylpentanoic acid.

6. A method according to claim 1, wherein the compound
2-propylpentanoic acid,
2-propylheptanoic acid,
2-propylhexanoic acid,
2-propyldecanoic acid,
2-propyloctanoic acid,
2-propyinonanoic acid,
4-methyl-2-propylpentanoic acid,
5-methyl-2-propylhexanoic acid,
7-methyl-2-propyloctanoic acid,
6-methyl-2-propylheptanoic acid,
5-ethyl-2-propylheptanoic acid,
55-ethyl-2-propylheptanoic acid,
5,-dimtheyl-2propylhpexanoic acid,
6,6-dimethyl-2-propylheptanoic acid,
2-ethylhexanoic acid, or
2-chloro-2-propyl pentanoic acid.

7. A method according to claim 1, wherein the compound
7-chloro-2-propylheptanoic acid,
2-benzylpentanoic acid,
2-(3-phenylpropyl)pentanoic acid,
6-phenyl-2-propylhexanoic acid,
5-phenoxy-2-propylpentanoic acid,
2-cyclohexylmethylpentanoic acid,
2-(2-cyclohexylethyl)pentanoic acid,
5-cyclohexyl-2-propylpentanoic acid,
2-(2-ethoxyethyl)pentanoic acid,
2-(2-methoxyethyl)pentanoic acid,
5-methoxy-2-propylpentanoic acid,
5-ethoxy-2-propylpentanoic acid,
6-methoxy-2-propylhexanoic acid,
2-phenylpentanoic acid,
2-phenoxypentanoic acid,
2-cycl openthylpentanoic acid,
2-cyclohexylpentanoic acid,
2-pentylthiopentanoic acid,
2-propyl-4-pentenoic acid,
2-propyl-7-octenoic acid,
2-propoxypentanoic acid,
2-ethoxypentano ic acid,
2-butoxypentanoic acid,
2-pentyloxypentanoic acid,
2-hexyloxypentanoic acid,
2-propyl-2-pentenoic acid.

8. The method of claim 1, wherein said compound of the formula (X) is 2-propylpentanoic acid.

9. The method of claim 1, wherein said compound of the formula (X) is 2-propyloctanoic acid.

10. A method according to claim 1, wherein the disease is Alzheimer's disease, amyotrophic lateral sclerosis, progressive supra nuclear palsy, olive-ponto-cerebellar atrophy, neuronal dysfunction by stroke or traumatic injury, multiple sclerosis, astrocytoma, meningitis, brain abscess, Creutzfeldt-Jakob disease, or AIDS dementia.

* * * * *